United States Patent
Brown et al.

(10) Patent No.: US 6,391,561 B1
(45) Date of Patent: May 21, 2002

(54) PROTEIN THAT ENHANCES EXPRESSION OF POTASSIUM CHANNELS ON CELL SURFACES AND NUCLEIC ACIDS THAT ENCODE THE SAME

(75) Inventors: Arthur M. Brown, Brecksville; Barbara A. Wible, Cleveland; Qing Yang, S. Euclid, all of OH (US)

(73) Assignee: The MetroHealth System, Cleveland, OH (US)

( * ) Notice: Subject to any disclaimer, the term of this patent is extended or adjusted under 35 U.S.C. 154(b) by 0 days.

(21) Appl. No.: 09/712,495

(22) Filed: Nov. 14, 2000

Related U.S. Application Data

(62) Division of application No. 09/062,440, filed on Apr. 17, 1998, now Pat. No. 6,207,422.

(51) Int. Cl.[7] .......................... C12Q 1/68; G01N 33/53; C12P 19/34; C07H 19/00; C07H 21/04
(52) U.S. Cl. .......................... 435/6; 435/7.1; 435/91.1; 435/91.2; 536/22.1; 536/23.1; 536/24.3; 536/24.31; 536/24.32; 536/24.33; 530/350
(58) Field of Search .......................... 435/6, 7.1, 91.1, 435/91.2; 536/22.1, 23.1, 23.5, 24.3, 24.31, 24.32, 24.33; 530/350

(56) References Cited

U.S. PATENT DOCUMENTS

| | | |
|---|---|---|
| 5,492,825 A | 2/1996 | Jan et al. |
| 5,670,335 A | 9/1997 | Jan et al. |
| 5,756,669 A | 5/1998 | Bischoff et al. |
| 5,856,449 A | 1/1999 | Groppi, Jr. et al. |
| 5,882,873 A | 3/1999 | Bienkowski et al. |
| 6,207,422 B1 * | 3/2001 | Brown et al. ............... 435/91.1 |

FOREIGN PATENT DOCUMENTS

WO    95/31544    11/1995

OTHER PUBLICATIONS

"Cloning and Characterization of Gu/RH–II Binding Protien" by Valdez, et al., *Biochemical and Biophysical Research Communications*, 234, 335–340 (1997).
"Specific Inhibition of Stat3 Signal Transduction by PIAS3" by Chung, et al., *Science*, vol. 278, Dec. 5, 1997, pp. 1803–1805.
"Miz1, a novel zinc finger transcription factor that interacts with Msx2 and enhances its affinity for DNA" by Wu, et al., *Mechanisms of Development*, 65 (1997) 3–17.
"Cloning and Expression of a Novel K+ Channel Regulatory Protein, KChAP" by Wible, et al., *The Journal of Biological Chemistry*, vol. 273, 1998, pp. 1–7.

* cited by examiner

*Primary Examiner*—Jeffrey Siew
(74) *Attorney, Agent, or Firm*—Calfee, Halter & Griswold LLP

(57) ABSTRACT

The present invention provides polynucleotides that encode a protein, designated herein as K+ Channel Associated Protein or "KChAP". It has been determined that expressing polynucleotides that encode KChAP in host cells, along with polynucleotides that encode the Kvα channel subunit Kv 2.1, the Kvα channel subunit Kv 2.2, the Kvα channel subunit Kv 1.3, or the Kvα channel subunit Kv 4.3, increases the number of Kv2.1, Kv 2.2, Kv1.3 or Kv4.3 channels, respectively, in the plasma membrane of such cells. The present invention also relates to a method of making cells that have increased numbers of Kv channels on the plasma membranes thereof and to a method of using such cells as model systems for studying the effect of pharmacological agents on Kv channels, particularly on Kv2.1, Kv 2.2, Kv 1.3, and Kv 4.3 channels. The present invention also relates to the protein KChAP.

10 Claims, 11 Drawing Sheets

Fig. 2A

```
     atgaagatcaaagaactttaccgcaggcgctttccccggaagaccctggggccttccgat
  1  ---------+---------+---------+---------+---------+---------+  60
     M  K  I  K  E  L  Y  R  R  R  F  P  R  K  T  L  G  R  S  D   -
```

```
     ctctctttgctctctttgcccccctggcacctctcctgtaggctcccccagcccccttgct
 61  ---------+---------+---------+---------+---------+---------+  120
     L  S  L  L  S  L  P  P  G  T  S  P  V  G  S  P  S  P  L  A   -
                                          A
                                          p
                                          a
                                          I
```

```
     tccattcctcccaccctcctgacccctggcaccttgctgggccctaagcgtgaggtggac
121  ---------+---------+---------+---------+---------+---------+  180
     S  I  P  P  T  L  L  T  P  G  T  L  L  G  P  K  R  E  V  D   -
                                    A
                                    a
                                    t
                                    I
                                    I
```

```
     atgcaccctcctctgccccagcctgtgcaccctgacgtcaccatgaaaccactgcccttc
181  ---------+---------+---------+---------+---------+---------+  240
     M  H  P  P  L  P  Q  P  V  H  P  D  V  T  M  K  P  L  P  F   -
                           E
                           a
                           g
                           I
```

```
     tacgaagtctacggagagctcatccggccgaccacccttgcgtccacctccagtcagagg
241  ---------+---------+---------+---------+---------+---------+  300
     Y  E  V  Y  G  E  L  I  R  P  T  T  L  A  S  T  S  S  Q  R   -
                                             P
                                             v         p
                                             u         s
                                             I         t
                                             I         I
```

```
     tttgaggaagcccactttacctttgcactcactccccagcagctgcagcagattctcaca
301  ---------+---------+---------+---------+---------+---------+  360
     F  E  E  H  H  F  T  F  A  L  T  P  Q  Q  L  Q  Q  I  L  T   -
```

Fig. 2B

```
      tccagggaggttctgccaggagccaagtgcgattataccatacaagtgcagctcaggttc
361   ---------+---------+---------+---------+---------+---------+  420
      S   R   E   V   L   P   G   A   K   C   D   Y   T   I   Q   V   Q   L   R   F    -
                                      P
                                      v
                                      u
                                      I
                                      I
      tgtctctgtgagaccagctgcccccaggaggactatttccccctaacctctttgtcaag
421   ---------+---------+---------+---------+---------+---------+  480
      C   L   C   E   T   S   C   P   Q   E   D   Y   F   P   P   N   L   F   V   K    -
                                          B
                                          s
                                          t
                                          E
                                          I
                                          I
      gttaatgggaaactctgcccctgccgggttacctccctccaaccaagaatggagctgag
481   ---------+---------+---------+---------+---------+---------+  540
      V   N   G   K   L   C   P   L   P   G   Y   L   P   P   T   K   N   G   A   E    -
              S
              t
              u
              I
      cccaagaggcctagtcgtccaatcaacatcacacccctggctcgtctctcagccactgtt
541   ---------+---------+---------+---------+---------+---------+  600
      P   K   R   P   S   R   P   I   N   I   T   P   L   A   R   L   S   A   T   V    -
                              H
                              p
                              a
                              I
      cccaacaccatagtggttaactggtcatctgagtttggacggaattactccttgtctgtg
601   ---------+---------+---------+---------+---------+---------+  660
      P   N   T   I   V   V   N   W   S   S   E   F   G   R   N   Y   S   L   S   V    -
```

Fig. 2C

```
                                                                   B
                             p                                     s
                             s                                     a
                             t                                     W
                             I                                     I
    tacctggtgaggcagttgactgcagggaccctgctacaaaagctcagagccaagggtatc
661 ---------+---------+---------+---------+---------+---------+  720
    Y  L  V  R  Q  L  T  A  G  T  L  L  Q  K  L  R  A  K  G  I   -

A
                   v
                   a
                   I
    cggaatccagaccattcccgagcactgatcaaggagaaattgactgctgaccccgacagt
721 ---------+---------+---------+---------+---------+---------+  780
    R  N  P  D  H  S  R  A  L  I  K  E  K  L  T  A  D  P  D  S   - gaagtggctactacaagtctccgggtgtcactcatgtgcccgctggggaagatgcgcctg
781 ---------+---------+---------+---------+---------+---------+  840
    E  V  A  T  T  S  L  R  V  S  L  M  C  P  L  G  K  M  R  L   -

P
                                       s
                                       t
                                       I
    actgtcccatgccgcgctctcacctgtgcccacctgcagagtttcgatgctgccctttat
841 ---------+---------+---------+---------+---------+---------+  900
    T  V  P  C  R  A  L  T  C  A  H  L  Q  S  F  D  A  A  L  Y   - ctacagatgaatgagaaaaagccaacatggacgtgccctgtgtgtgacaagaaggctccc
901 ---------+---------+---------+---------+---------+---------+  960
    L  Q  M  N  E  K  K  P  T  W  T  C  P  V  C  D  K  K  A  P   - tatgagtcactgattattgatggtttattcatggaaattcttaattcctgttcggattgt
961 ---------+---------+---------+---------+---------+---------+  1020
    Y  E  S  L  I  I  D  G  L  F  M  E  I  L  N  S  C  S  D  C   -

P              B
                 f              a
                 l              m
                 M              H
                 I              I
    gatgagatccagttcatggaagatggatcctggtgtccaatgaaacccaagaaggaggca
1021---------+---------+---------+---------+---------+---------+  1080
       D  E  I  Q  F  M  E  D  G  S  W  C  P  M  K  P  K  K  E  A  -
```

Fig. 2D

```
                           P
                           f
                           l
                           M
                           I
       tccgaggtttgccccccaccagggtatgggctggatggtctccagtatagcccagtccag
1081 ---------+---------+---------+---------+---------+---------+  1140
       S  E  V  C  P  P  P  G  Y  G  L  D  G  L  Q  Y  S  P  V  Q   - gagggaaatcagtcagagaataagaagagggttgaagtcattgacttgacaatcgaaagc
1141 ---------+---------+---------+---------+---------+---------+  1200
       E  G  N  Q  S  E  N  K  K  R  V  E  V  I  D  L  T  I  E  S   -

B
                    g
                    l
                    I
                    I
       tcatcagatgaggaagatctgccccccaccaagaagcactgccctgttacctcggctgcc
1201 ---------+---------+---------+---------+---------+---------+  1260
       S  S  D  E  E  D  L  P  P  T  K  K  H  C  P  V  T  S  A  A   -

B
                              s
                              t
                              E
                              I
                              I
       attccagcccttcctggaagcaaaggagccctgacctctggtcaccagccgtcttcggtg
1261 ---------+---------+---------+---------+---------+---------+  1320
       I  P  A  L  P  G  S  K  G  A  L  T  S  G  H  Q  P  S  S  V   - ctgcggagccctgcaatgggtacactgggcagtgatttcctgtctagtctcccactacat
1321 ---------+---------+---------+---------+---------+---------+  1380
       L  R  S  P  A  M  G  T  L  G  S  D  F  L  S  S  L  P  L  H   - gagtacccacctgccttcccgctgggggctgacatccaaggtttagatttatttctttc
1381 ---------+---------+---------+---------+---------+---------+  1440
       E  Y  P  P  A  F  P  L  G  A  D  I  Q  G  L  D  L  F  S  F   - cttcagactgagagtcagcactacagcccttcagttatcacttcactagatgagcaggac
1441 ---------+---------+---------+---------+---------+---------+  1500
       L  Q  T  E  S  Q  H  Y  S  P  S  V  I  T  S  L  D  E  Q  D   -
```

Fig. 2E

```
                                                P
                                                f         A
                                                l         p
                                                M         a
                                                I         I
        accctt ggccacttct tccaattccg gggaacccct ccccacttcc tgggccactg gcc
1501 ----------+----------+----------+----------+----------+----------+ 1560
      . T  L  G  H  F  F  Q  F  R  G  T  P  P  H  F  L  G  P  L  A     - cccacattgg ggagctctca ccgcagcgcc actccagcac ccgctcctgg ccgtgtcagc
1561 ----------+----------+----------+----------+----------+----------+ 1620
         P  T  L  G  S  S  J  R  S  A  T  P  A  P  A  P  G  R  V  S    -

B
                                                                  s
                                                                  a
                                                                  W
                                                                  I
        agcattgtgg ctcctggga gttccttgag ggaagggcat ggaggacccc tgccttccggt
1621 ----------+----------+----------+----------+----------+----------+ 1680
         S  I  V  A  P  G  S  S  L  R  E  G  H  G  G  P  L  P  S  G    -

A
                                a
                                t
                                I
                                I
        ccctctttga ctggctgtcg gtcagacgtc atttccttgg actga
1681 ----------+----------+----------+----------+----- 1725
         P  S  L  T  G  C  R  S  D  V  I  S  L  D  *       -
```

Enzymes that do cut:

| AatII | ApaI  | AvaI | BamHI | BglII | BsaWI | BstEII | EagI |
|-------|-------|------|-------|-------|-------|--------|------|
| HpaI  | PflMI | PstI | PvuII | StuI  |       |        |      |

Enzymes that do not cut:

| AgeI  | AseI  | BbrPI | BfrI   | BsaBI | BsmI    | BssHII | BstbI |
|-------|-------|-------|--------|-------|---------|--------|-------|
| BstXI | ClaI  | DraI  | DraIII | EcoRI | HindIII | KpnI   | MluI  |
| NarI  | NcoI  | NdeI  | NheI   | NotI  | NruI    | NsiI   | PmlI  |
| PvuI  | SacII | SalI  | SauI   | ScaI  | SfiI    | SmaI   | SnaBI |
| SpeI  | SspI  | XbaI  | XhoI   |       |         |        |       |

Fig. 3A

```
                                                             A
                                                             p
                                                             a
                                                             I
     atgaagatcaaagagctttaccgacgacgctttccccggaagaccctggggccctctgat
  1  ---------+---------+---------+---------+---------+---------+  60
     M  K  I  K  E  L  Y  R  R  R  F  P  R  K  T  L  G  P  S  D   - ctctcccttctctctttgcccctggcacctctcctgtaggctcccctggtcctctagct
 61  ---------+---------+---------+---------+---------+---------+  120
     L  S  L  L  S  L  P  P  G  T  S  P  V  G  S  P  G  P  L  A   -

A
                                          p
                                          a
                                          I
     cccattcccccaacgctgttggcccctggcaccctgctgggccccaagcgtgaggtggac
121  ---------+---------+---------+---------+---------+---------+  180
     P  I  P  P  T  L  L  A  P  G  T  L  L  G  P  K  R  E  V  D   - atgcacccccctctgccccagcctgtgcaccctgatgtcaccatgaaaccattgcccttc
181  ---------+---------+---------+---------+---------+---------+  240
     M  H  P  P  L  P  Q  P  V  H  P  D  V  T  M  K  P  L  P  F   - tatgaagtctatggggagctcatccggcccaccacccttgcatccacttctagccagcgg
241  ---------+---------+---------+---------+---------+---------+  300
     Y  E  V  Y  G  E  L  I  R  P  T  T  L  A  S  T  S  S  Q  R   - tttgaggaagcgcactttacctttgccctcacaccccagcaagtgcagcagattcttaca
301  ---------+---------+---------+---------+---------+---------+  360
     F  E  E  A  H  F  T  F  A  L  T  P  Q  Q  V  Q  Q  I  L  T   - tccagagaggttctgccaggagccaaatgtgattataccatacaggtgcagctaaggttc
361  ---------+---------+---------+---------+---------+---------+  420
     S  R  E  V  L  P  G  A  K  C  D  Y  T  I  Q  V  Q  L  R  F   -

P
                           v
                           u
                           I
                           I
     tgtctctgtgagaccagctgccccccaggaagattattttcccccaacctctttgtcaag
421  ---------+---------+---------+---------+--------+---------+  480
     C  L  C  E  T  S  C  P  Q  E  D  Y  F  P  P  N  L  F  V  K   -
```

Fig. 3B

```
                          B
                          s
                          t
                          E
                          I
                          I
     gttaatgggaaactgtgcccctgccgggttaccttccccaaccaagaatggggccgag
481  ---------+---------+---------+---------+---------+---------+  540
     V  N  G  K  L  C  P  L  P  G  Y  L  P  P  T  K  N  G  A  E   - cccaagaggcccagccgccccatcaacatcacacccctggctcgactctcagccactgtt
541  ---------+---------+---------+---------+---------+---------+  600
     P  K  R  P  S  R  P  I  N  I  T  P  L  A  R  L  S  A  T  V   - cccaacaccattgtggtcaattggtcatctgagttcggacggaattactccttgtctgtg
601  ---------+---------+---------+---------+---------+---------+  660
     P  N  T  I  V  V  N  W  S  S  E  F  G  R  N  Y  S  L  S  V   -

B
                   P                                    s
                   s                                    a
                   t                                    W
                   I                                    I
     tacctggtgaggcagttgactgcaggaacccttctacaaaaactcagagcaaagggtatc
661  ---------+---------+---------+---------+---------+---------+  720
     Y  L  V  R  Q  L  T  A  G  T  L  L  Q  K  L  R  A  K  G  I   - cggaacccagaccactcgcgggcactgatcaaggagaaattgactgctgaccctgacagt
721  ---------+---------+---------+---------+---------+---------+  780
     R  N  P  D  H  S  R  A  L  I  K  E  K  L  T  A  D  P  D  S   - gaggtggccactacaagtctccgggtgtcactcatgtgcccgctagggaagatgcgcctg
781  ---------+---------+---------+---------+---------+---------+  840
     E  V  A  T  T  S  L  R  V  S  L  M  C  P  L  G  K  M  R  L   -

P
                                    s
                                    t
                                    I
     actgtcccttgtcgtgccctcacctgtgcccacctgcagagcttcgatgctgccctttat
841  ---------+---------+---------+---------+---------+---------+  900
     T  V  P  C  R  A  L  T  C  A  H  L  Q  S  F  D  A  A  L  Y   - ctacagatgaatgagaagaagcctacatggacatgtcctgtgtgtgacaagaaggctccc
901  ---------+---------+---------+---------+---------+---------+  960
     L  Q  M  N  E  K  K  P  T  W  T  C  P  V  C  D  K  K  A  P   -
```

Fig. 3C

```
      tatgaatctcttatcattgatggtttatttatggagattcttagttcctgttcagattgt
 961  ---------+---------+---------+---------+---------+---------+  1020
       Y  E  S  L  I  I  D  G  L  F  M  E  I  L  S  S  C  S  D  C   -

P              B
                              f              a
                              l              m
                              M              H
                              I              I
      gatgagatccaattcatggaagatggatcctggtgcccaatgaaacccaagaaggaggca
1021  ---------+---------+---------+---------+---------+---------+  1080
       D  E  I  Q  F  M  E  D  G  S  W  C  P  M  K  P  K  K  E  A   -

P
                                       f
                                       l
                                       M
                                       I
      tctgaggtttgccccccgccagggtatgggctggatggcctccagtacagcccagtccag
1081  ---------+---------+---------+---------+---------+---------+  1140
       S  E  V  C  P  P  P  G  Y  G  L  D  G  L  Q  Y  S  P  V  Q   - ggggagatccatcagagaataagaagaaggtcgaagttattgacttgacaatagaaagc
1141  ---------+---------+---------+---------+---------+---------+  1200
       G  G  D  P  S  E  N  K  K  K  V  E  V  I  D  L  T  I  E  S   -

P
                                                      v
                                                      u
                                                      I
                                                      I
      tcatcagatgaggaggatctgccccctaccaagaagcactgttctgtcacctcagctgcc
1201  ---------+---------+---------+---------+---------+---------+  1260
       S  S  D  E  E  D  L  P  P  T  K  K  H  C  S  V  T  S  A  A   - atcccggccctacctggaagcaaaggagtcctgacatctggccaccagccatcctcggtg
1261  ---------+---------+---------+---------+---------+---------+  1320
       I  P  A  L  P  G  S  K  G  V  L  T  S  G  H  Q  P  S  S  V   - ctaaggagccctgctatgggcacgttgggtggggatttcctgtccagtctcccactacat
1321  ---------+---------+---------+---------+---------+---------+  1380
       L  R  S  P  A  M  G  T  L  G  G  D  F  L  S  S  L  P  L  H   - gagtacccacctgccttcccactgggagccgacatccaaggtttagatttattttcattt
1381  ---------+---------+---------+---------+---------+---------+  1400
       E  Y  P  P  A  F  P  L  G  A  D  I  Q  G  L  D  L  F  S  F   -
```

Fig. 3D

```
     cttcagacagagagtcagcactatggcccctctgtcatcacctcactagatgaacaggat
1441 ---------+---------+---------+---------+---------+---------+ 1500
      L  Q  T  E  S  Q  H  Y  G  P  S  V  I  T  S  L  D  E  Q  D  -
                                                          A
                                                          p
                                                          a
                                                          I
     gcccttggccacttcttccagtaccgagggaccccttctcactttctgggcccactggcc
1501 ---------+---------+---------+---------+---------+---------+ 1560
      A  L  G  H  F  F  Q  Y  R  G  T  P  S  H  F  L  G  P  L  A  -
                             P                 N
                             s                 a
                             t                 r
                             I                 I
     cccacgctggggagctcccactgcagcgccactccggcgccccctcctggccgtgtcagc
1561 ---------+---------+---------+---------+---------+---------+ 1620
      P  T  L  G  S  S  H  C  S  A  T  P  A  P  P  P  G  R  V  S  -
                                                             S
                                                             a
                                                             u
                                                             I
     agcattgtggcccctggggggggccttgagggagggcatggaggaccctgccctcaggt
1621 ---------+---------+---------+---------+---------+---------+ 1680
      S  I  V  A  P  G  G  A  L  R  E  G  H  G  G  P  L  P  S  G  - ccctctttgactggctgtcggtcagacatcatttccctggactga
1681 ---------+---------+---------+---------+----- 1725
      P  S  L  T  G  C  R  S  D  I  I  S  L  D  *  -
```

Enzymes that do cut:

| ApaI | BamHI | BsaWI | BstEII | NarI | PflMI | PstI | PvuII |
|------|-------|-------|--------|------|-------|------|-------|
| SauI |       |       |        |      |       |      |       |

Enzymes that do not cut:

| AatII | AgeI    | AseI  | AvaI  | BbrPI | BfrI  | BglII  | BsaBI |
|-------|---------|-------|-------|-------|-------|--------|-------|
| BsmI  | BssHII  | BstBI | BstXI | ClaI  | DraI  | DraIII | EagI  |
| EcoRI | HindIII | HpaI  | KpnI  | MluI  | NcoI  | NdeI   | NheI  |
| NotI  | NruI    | NsiI  | PmlI  | PvuI  | SacII | SalI   | ScaI  |
| SfiI  | SmaI    | SnaBI | SpeI  | SspI  | StuI  | XbaI   | XhoI  |

Fig. 4

```
  1 MKIKELYRRRFPRKTLGPSDLSLLSLPPGTSPVGSPGPLAPIPPTLLAPG  50
    ||||||||||||||||||||||||||||||||||:|||.|||||||.||
  1 MKIKELYRRRFPRKTLGPSDLSLLSLPPGTSPVGSPSPLASIPPTLLTPG  50

51 TLLGPKREVDMHPPLPQPVHPDVTMKPLPFYEVYGELIRPTTLASTSSQR 100
    |||||||||||||||||||||||||||||||||||||||||||||||||
 51 TLLGPKREVDMHPPLPQPVHPDVTMKPLPFYEVYGELIRPTTLASTSSQR 100

101 FEEAHFTFALTPQQVQQILTSREVLPGAKCDYTIQVQLRFCLCETSCPQE 150
    |||||||||||||:|||||||||||||||||||||||||||||||||||
101 FEEAHFTFALTPQQLQQILTSREVLPGAKCDYTIQVQLRFCLCETSCPQE 150

151 DYFPPNLFVKVNGKLCPLPGYLPPTKNGAEPKRPSRPINITPLARLSATV 200
    |||||||||||||||||||||||||||||||||||||||||||||||||
151 DYFPPNLFVKVNGKLCPLPGYLPPTKNGAEPKRPSRPINITPLARLSATV 200

201 PNTIVVNWSSEFGRNYSLSVYLVRQLTAGTLLQKLRAKGIRNPDHSRALI 250
    |||||||||||||||||||||||||||||||||||||||||||||||||
201 PNTIVVNWSSEFGRNYSLSVYLVRQLTAGTLLQKLRAKGIRNPDHSRALI 250

251 KEKLTADPDSEVATTSLRVSLMCPLGKMRLTVPCRALTCAHLQSFDAALY 300
    |||||||||||||||||||||||||||||||||||||||||||||||||
251 KEKLTADPDSEVATTSLRVSLMCPLGKMRLTVPCRALTCAHLQSFDAALY 300

301 LQMNEKKPTWTCPVCDKKAPYESLIIDGLFMEILSSCSDCDEIQFMEDGS 350
    ||||||||||||||||||||||||||||||||||.||||||||||||||
301 LQMNEKKPTWTCPVCDKKAPYESLIIDGLFMEILNSCSDCDEIQFMEDGS 350

351 WCPMKPKKEASEVCPPPGYGLDGLQYSPVQGGDPSENKKKVEVIDLTIES 400
    |||||||||||||||||||||||||||||||:|:.||||:|||||||||
351 WCPMKPKKEASEVCPPPGYGLDGLQYSPVQEGNQSENKKRVEVIDLTIES 400

401 SSDEEDLPPTKKHCSVTSAAIPALPGSKGVLTSGHQPSSVLRSPAMGTLG 450
    |||||||||||.|||||||||||||||||.|||||||||||||||||||
401 SSDEEDLPPTKKHCPVTSAAIPALPGSKGALTSGHQPSSVLRSPAMGTLG 450

451 GDFLSSLPLHEYPPAFPLGADIQGLDLFSFLQTESQHYGPSVITSLDEQD 500
    :||||||||||||||||||||||||||||||||||||||:|||||||||
451 SDFLSSLPLHEYPPAFPLGADIQGLDLFSFLQTESQHYSPSVITSLDEQD 500

501 ALGHFFQYRGTPSHFLGPLAPTLGSSHCSATPAPPPGRVSSIVAPGGALR 550
    .||||||:||||.|||||||||||||| ||||||:|||||||||||:.||
501 TLGHFFQFRGTPPHFLGPLAPTLGSSHRSATPAPAPGRVSSIVAPGSSLR 550

551 EGHGGPLPSGPSLTGCRSDIISLD* 575
    |||||||||||||||||||:|||||
551 EGHGGPLPSGPSLTGCRSDVISLD* 575
```

PROTEIN THAT ENHANCES EXPRESSION OF POTASSIUM CHANNELS ON CELL SURFACES AND NUCLEIC ACIDS THAT ENCODE THE SAME

CROSS-REFERENCE TO RELATED APPLICATIONS

This application is a divisional of the commonly assigned, U.S. patent application Ser. No.: 09/062,440, filed on, Apr. 17, 1998, which issued as U.S. Pat. No. 6,207,422 B1; on Mar. 27, 2001.

This invention was made in art with government support under grants HL-57416, HL-55404, HL-36930, and NS-23877 from the National Institutes of Health. The government has certain rights in the invention.

BACKGROUND OF THE INVENTION

The electrical properties of excitable cells are determined in large part by the voltage-gated $K^+$ channels, i.e., "Kv channels", present on the plasma membrane of such cells. Kv channels are also important in many nonexcitable cells where they contribute to diverse processes such as volume regulation, hormone secretion, and activation by mitogens. At least 50 different Kv channel genes have been identified, and most have been assigned to one of the following four major subfamilies: Kv1, Kv2, Kv3, and Kv4. Each Kv channel gene encodes a single pore-forming subunit, referred to as the α-subunit. Functional Kv channels are formed by the tetrameric association of individual α-subunits. With multiple Kvα proteins that assemble as multi-subunit heteromeric complexes, there may be hundreds of functionally distinct Kv channels.

Kv channels, either functioning or malfunctioning, are implicated in many disease states including cardiac arrhythmias, hypertension, angina, asthma, diabetes, renal insufficiency, urinary incontinence, irritable colon, epilepsy, cerebrovascular ischemia and autoimmune diseases. Accordingly, efforts are underway to identify and characterize pharmacological agents that alter the kinetics, gating or formation of Kv channels. The efficacy of such agents is determined by treating cells with such agents and measuring changes in current across the plasma membrane of the cells. Unfortunately, it is difficult to measure small changes in the current in most cells. It is also difficult to determine whether a pharmacological agent alters current flow through a specific Kv channel. Accordingly, it is desirable to have methods and tools which can be used to regulate the numbers and types of Kv channels on the plasma membrane of cells. It is also desirable to have new research tools that can be used for examining the assembly and synthesis of Kv channels.

SUMMARY OF THE INVENTION

The present invention provides novel polynucleotides that encode a novel protein, designated herein as K+ Channel Associated Protein or "KChAP". It has been determined that expressing polynucleotides that encode KChAP in host cells, along with polynucleotides that encode the Kvα channel subunit Kv 2.1, the Kvα channel subunit Kv 2.2, the Kvα channel subunit Kv 1.3, or the Kvα channel subunit Kv 4.3, increases the number of Kv2.1, Kv 2.2, Kv1.3 or Kv4.3 channels, respectively, in the plasma membrane of such cells. Accordingly, KChAP polynucleotides are useful for making cells that have increased numbers of Kv channels on the cellular plasma membrane. Such cells are useful model systems for studying the effect of pharmacological agents on Kv channels, particularly on Kv2.1, Kv 2.2, Kv 1.3, and Kv 4.3 channels.

The present invention also relates to the novel protein KChAP. During formation of Kv channels, KChAP binds to the Kvα channel subunits Kv2.1, Kv2.2, Kv1.3, and Kv4.3 within the cytoplasm of the cell. KChAP also binds to the Kvα channel subunits Kv1.2, Kv 1.4, Kv1.5 and Kv 3.1 and to Kvβ subunits. Accordingly, KChAP and the antibodies that are immunospecific for KChAP are useful research tools for monitoring the interaction between diverse Kvα channel subunits and KChAP and for monitoring the interaction between Kvα subunits and Kvβ subunits.

BRIEF DESCRIPTION OF THE FIGURES

FIG. 2 shows a cDNA sequence, SEQ ID NO: 1, that encodes rat KChAP, and the predicted amino acid sequence, SEQ ID NO: 2, of the KChAP protein encoded by the rat cDNA;

FIG. 3 shows a cDNA sequence, SEQ ID NO: 3, that encodes human KChAP, and the predicted amino acid sequence, SEQ ID NO: 4, of the KChAP protein encoded by the human cDNA;

FIG. 4 provides a comparison of the amino acid sequences of rat KChAP SEQ ID No: 2, and human KChAP SEQ ID No: 2. The double dots between the sequences identify highly conserved amino acids, i.e., amino acids that are similar in size, hydrophobicity, and charge. The single dot between the aligned amino acid sequences identify amino acids that are less highly conserved.

DETAILED DESCRIPTION OF THE INVENTION

The KChAP Protein

Figure 1:
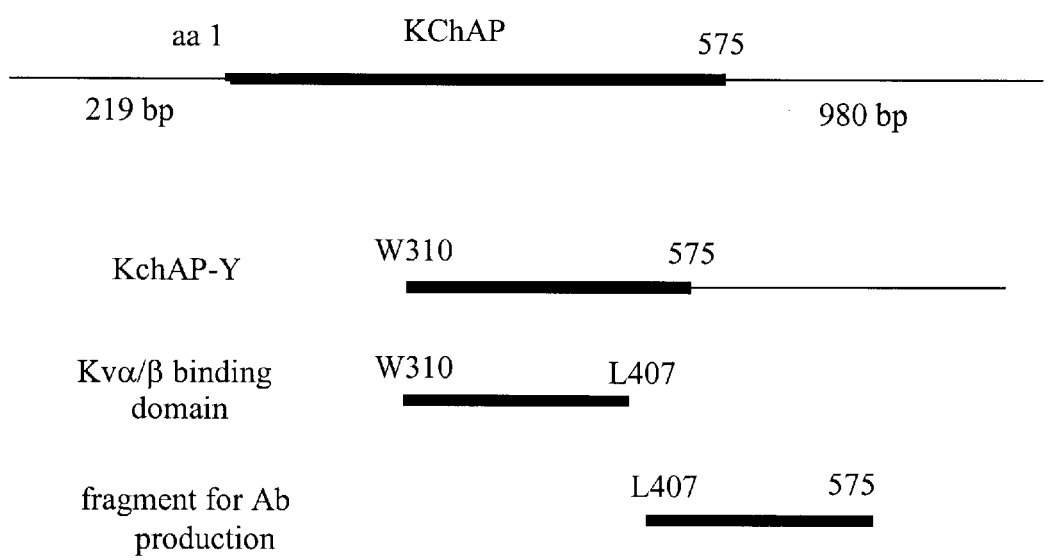
FIG. 1 is a schematic representation of a full-length cDNA that encodes KChAP and partial fragments thereof. The open reading frame is flanked by 219 base pairs of untranslated sequence on the 5' end, and 980 base pairs of untranslated sequence on the 3' end as indicated by the thin lines. KChAP-Y depicts the partial clone that was originally isolated in the yeast two-hybrid screen. KChAP-Y extends from amino acid W310 through the poly A tail at the 3' end. The domain on KChAP that binds to Kvα subunits and to Kvβ subunits, hereinafter referred to as the "Kvα/Kvβ binding domain", has been localized to the region between amino acids W310 and L407.

The present invention provides a unique protein KChAP. The mature form of KChAP has a calculated molecular weight of about 62.4 kDa. In one embodiment the human KChAP protein has the amino acid sequence shown in FIG. 3 (SEQ ID NO: 4). In one embodiment the rat KChAP protein has the amino acid sequence shown in FIG. 2 (SEQ ID NO: 2).

The present invention also relates to allelic variants or derivatives of the amino acid sequences shown in FIGS. 2 and 3. In addition to naturally occurring allelic forms of the protein, the KChAP protein as described herein embraces non-naturally occurring derivatives of the KChAP protein where one or more of the amino acids have been replaced by conservative amino acid residues, typically by using direct synthesis or recombinant techniques. The present invention also relates to allelic variants or derivatives of the KChAP that have an amino acid sequence identity of at least 85%, more preferably at least 90%, and most preferably of at least 95% with the amino acid sequences shown in FIG. 2 or FIG. 3, provided however, that the derivative is capable of binding to the N-termini of the Kvα subunits Kv 2.1, Kv2.2, Kv 1.3, Kv4.3 and to the C-terminus of Kvβ 1.2.

In another aspect, the present invention relates to an isolated peptide which comprises the domain of KChAP that binds to Kvα subunits, particularly the Kvα subunits Kv 2.1, Kv2.2, Kv4.3 and to Kvβ subunits, particularly Kvβ 1.2. Such domain is hereinafter referred to as the "Kvα/Kvβ binding domain". As used herein, peptide means a fragment of the KChAP protein and accordingly is smaller and comprises fewer amino acids than the KChAP protein. In one embodiment, this peptide comprises the amino acid sequence, SEQ ID NO: 5, extending from T309 through L407 as shown in FIG. 2 and the amino acid sequence, SEQ ID NO: 7, extending from T309 through L407 as shown in FIG. 3. The present invention also relates to allelic variants or derivatives of the amino acid sequence set forth in SEQ ID NO's: 5 and 7.

In another aspect, the present invention relates to an isolated peptide which comprises the C terminal domain of the KChAP protein, i.e., the last 160 to 170 amino acids of the KChAP protein. In one embodiment, the peptide comprises the amino acid sequence set forth in SEQ ID NO: 8. In another embodiment, the peptide comprises the amino acid sequence set forth in SEQ. ID NO: 9. In another embodiment, the peptide is a variant of the C terminal domain of the rat KChAP protein and the human KChAP protein and comprises:

(a) a Kvα/Kvβ binding domain having the following sequence:
WTCPVCDKKA PYESLIIDGL FMEILXaSCSD CDEIQFMEDG SWCPMKPKKE ASEVCPPPGY GLDGLQYSPV QXaGXaXaSENKK XaVEV-IDLTIE SSSDEEDL, SEQ ID NO: 10,
wherein the Xa at position 25 is serine or asparagine, the Xa at position 72 is glycine or glutamic acid, the Xa at position 74 is aspartic acid or asparagine, the Xa at position 75 is proline or glutamine the Xa at position 80 is lysine or arginine; and (b) a C terminal domain having the following sequence:
PPTKKHCXaVT SAAIPALPGS KGXaLTSGHQP SSVLRSPAMG TL GXaDFLSSL PLHEYPPAFP LG ADIQGLDL FSFLQTESQH YXaPSVITSLD EQDXaLGHFFQ XARGTPXaHFLG PLAPTLGSSH XaS ATPAPXaPG RVSSIVAPGXa XaLREGHGGPL PSGPSLTGCR SDIXaSLD SEQ ID NO: 11;
wherein the Xa at position 8 is serine or proline, the Xa at position 23 is valine or alanine, the Xa at position 44 is glycine or serine, the Xa at position 82 is, glycine or serine, the Xa at position 94 is alanine or threonine, the Xa at position 101 is tyrosine or phenylalanine, the Xa at position 106 is serine or proline, the Xa at position 121 is cystine or arginine, the Xa at position 128 is proline or alanine, the Xa at position 140 or glycine or serine, the Xa at position 141 is alanine or serine, the Xa at position 164 is isoleucine or valine.

Such peptides are useful for producing antibodies that are immunospecific for KChAP.

The present invention also relates to fusion proteins wherein additional amino acids are fused to the KChAP protein or to the peptide fragments of KChAP. The additional amino acids are added at either the 3' end or 5' end of the protein or peptide, for example, to aid in purification of the protein or peptide. The KChAP proteins and peptides are provided in an isolated form.

KChAP is not a channel protein. KChAP binds with the N-termini of Kvα1 and Kvα2 subunits. Specifically, KChAP binds with the α subunits Kv 2.1, Kv 2.2, Kv 1.3, Kv 4.3, Kv1.2, Kv1.4, Kv1.5. KChAP also binds to Kvβ subunits, particularly Kvβ1 and its isoforms. Kvβ subunits are cytoplasmic proteins that form stable complexes with Kvβ1 subunits. Kβ subunits are strong modulators of Kv channels. The Kβ subunit, Kβ1.2 suppresses current in the Kv1.5 potassium channel; this effect is abolished by KChAP which binds the Kvβ1.2.

Preparing KChAP

KChAP may be synthetically produced by conventional peptide synthesizers. Preferably, KChAP is produced using cell-free translation systems and RNA molecules derived from DNA constructs that encode the KChAP protein. Alternatively, KChAP is made by transfecting host cells with expression vectors that comprise a DNA sequence that encodes the KChAP protein and then inducing expression of the protein in the host cells. For recombinant production, recombinant constructs comprising one or more of the sequences which encode KChAP are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

KChAP is expressed in suitable host cells, such as for example, mammalian cells, yeast, bacteria, or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the KChAP protein.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, high performance liquid chromatography (HPLC), and affinity chromatography may be used to isolate recombinant KChAP.

Preparation of Antibodies

Recombinant KChAP or portions thereof, i.e., KChAP peptides, are used as immunogens to produce antibodies immunospecific for wild-type KChAP. Preferably, the KChAP peptides have little sequence homology with the human Gu binding protein, whose amino acid sequence is about 50% homologous with the amino acid sequences shown in FIGS. 2 and 3. The term "immunospecific" means the antibodies have substantially greater affinity for KChAP than for other proteins. Such antibodies are generated using conventional techniques by administering KChAP or the portion thereof to an animal, preferably a nonhuman, more preferably a rabbit. Conventional protocols are also used to collect blood from the immunized animals and to isolate the serum and or the IgG fraction from the blood. For preparation of monoclonal antibodies, conventional hybridoma techniques are used.

Polyclonal serum to KChAP was made using a bacterial fusion protein comprising the C-terminal 167 amino acids of KChAP. i.e., from amino acid L407, fused to the maltose binding protein. The fusion protein was prepared by subcloning the C-terminal 167 amino acids of KChAP into pMAL-C2 vector from New England Biolabs. The resulting vector was used to transform E. coli. The fusion protein was isolated from transformed E. coli cells on an amylose resin and sent to Research Genetics, Inc. for generation of polyclonal sera using conventional techniques.

Antibodies to KChAP are useful analytical tools for monitoring the formation of Kv channels and for studying the intracellular association of KChAP with Kvα subunits and with Kvβ subunits. Such antibodies are also useful reagents for identifying the intracellular location of the interaction between KChAP and Kvα and Kvβ subunits. Such antibodies are also useful to isolate or identify cells expressing the KChAP protein and to purify KChAP from partially purified preparations by affinity chromatography.

The KChAP Polynucleotide

The present invention also provides polynucleotides that encode the KChAP protein and the KChAP peptides of the present invention, hereinafter referred to collectively as the "KChAP polynucleotides". The KChAP polynucleotide is single stranded or double stranded. The polynucleotide is a DNA or RNA molecule, preferably a DNA molecule, and comprises a sequence which codes for the KChAP protein, preferably the human KChAP protein, or fragments thereof. Optionally, the polynucleotide also comprises a leader sequence and encodes a KChAP protein which is processed and secreted from mammalian cells as the mature polypeptide. Polynucleotides encoding KChAP protein may also be fused in frame to a marker sequence which allows for purification of the KChAP protein such as the maltose binding protein, which binds to amylose resin. Polynucleotides encoding KChAP protein or KChAP peptide fragments may also be fused in frame to a marker sequence, such as c-myc, which encodes an epitope that allows for monitoring the intracellular location of KChAP using commercially available antibodies.

In one embodiment, the KChAP polynucleotide encodes for a KChAP protein comprising the amino acid sequence shown in FIG. 2, SEQ ID NO: 2. One example of a polynucleotide that encodes the protein of SEQ ID NO: 2, is depicted in FIG. 2, and set forth in SEQ ID NO: 1. In another embodiment, the polynucleotide encodes for a KChAP protein comprising the amino acid sequence shown in FIG. 3, SEQ ID NO: 4. One example of a polynucleotide that encodes the protein of SEQ ID NO: 4 is depicted in FIG. 3 and set forth in SEQ ID NO: 3. The present invention also relates to polynucleotides that encode an allelic variant of the proteins having the amino acid sequences shown in FIGS. 2 and 3.

In another embodiment, the polynucleotide encodes for variants of KChAP protein, wherein the variants have the following sequence:

MKIKELYRRR FPRKTLGPSD LSLLSLPPGT SPVG-SPXaPLA XaIPPTLLXaPG TLLGPKREVD MHP-PLPQPVH PDVTMKPLPF YEVYGELIRP TTLASTSSQR; FEEAHFTFAL TPQQXaQQILT SREVLPGAKC DYTIQVQLRF CLCETSCPQE; DYFPPNLFVK VNGKLCPLPG YLPPTKNGAE PKRPSRPINI TPLARLSATV; PNTIVVNWSS EFGRNYSLSV YLVRQLTAGT LLQKLRAKGI RNPDHSRALI; KEKLTADPDS EVATTSLRVS LMCPLGKMRL TVPCRALTCA HLQSFDAALY; LQMNEKKPTW TCPVCDKKAP YESLIIDGLF MEILXaSCSDC DEIQFMEDGS; WCPMKPKKEA SEVCPPPGYG LDGLQYSPVQ XaGXaPSENKKXa VEVIDLTIES; SSDEEDLPP TKKHCXaVTSA AIPALPGSKG XaLTSGHQPSS VLRSPAMGTLG; XaDFLSSLPLH EYPPAFPLGA DIQGLDLFSF LQTESQHYXaP SVITSLDEQD; XaLGHFFQXaRG TPXaHFLGPLA PTLGSSHXaSA TPAPXaPGRVS SIVAPGXaXaLR; EGHGGPLPSG PSLTGCRSDI XaSLD, SEQ ID NO: 6;
  wherein the amino acid Xa at position 37 is glycine or serine;
  the amino acid Xa at position 41 is proline or serine;
  the amino acid Xa at position 48 is alanine or threonine;
  the amino acid Xa at position 115 is valine or leucine;
  the amino acid Xa at position 335 is serine or asparagine;
  the amino acid Xa at position 381 is glycine or glutamic acid;
  the amino acid Xa at position 383 is aspartic acid or asparagine;
  the amino acid Xa at position 384 isoproline or glutamine;
  the amino acid Xa at position 390 is lysine or arganine;
  the amino acid Xa at position 416 is serine or proline;
  the amino acid Xa at position 431 is valine or alanine;
  the amino acid Xa at position 451 is glycine or serine;
  the amino acid Xa at position 489 is glycine or serine;
  the amino acid Xa at position 501 is alanine or threonine;
  the amino acid Xa at position 508 is tyrosine or phenylalanine;
  the amino acid Xa at position 513 is serine or proline;
  the amino acid Xa at position 528 is cysteine or arginine
  the amino acid Xa at position 535 is proline or alanine;
  the amino acid Xa at position 547 is glycine or serine;
  the amino acid Xa at position 548 is alanine or serine;
  the amino acid Xa at position 571 is isoleucine or valine.

The present invention further relates to polynucleotides which are complementary to sequences that have at least 85% identity, preferably 90% identity, more preferably 95% identity with the nucleotide sequences which encode the amino acid sequences shown in FIGS. 2 and 3 or SEQ ID NO: 6.

Preferably, the polynucleotides comprise a sequence which hybridizes under stringent conditions to sequences which encode the amino acid sequence shown in FIG. 2 and FIG. 3 or sequences which are complementary thereto. As herein used, the term "stringent conditions" means hybridization will occur if there is at least 95% and, preferably, at least 97% identity between the sequences. Preferably, the polynucleotide is provided in an isolated form.

The polynucleotides that encode the KChAP protein are useful for preparing cells that have increased numbers of Kv channels on their cell surface. The polynucleotides of the present invention are useful for preparing cells that have Kv channels formed from exogenous Kvα subunits. As used herein, "an exogenous Kvα subunit" means that the gene encoding the Kvα subunit is not normally expressed in the cell. Kvα subunits that are normally expressed in a cell are referred to as endogenous subunits. To prepare the cells, polynucleotides encoding KChAP and a Kvα subunit, an exogenous Kvα subunit, preferably are co-transfected or co-injected into host cells. Preferably, the cRNA molecules that encode KChAP and the Kvα subunit are coinjected with one pipette. Preferably, the Kvα subunit is a Kv2.1, Kv2.2, Kv1.3 or Kv4.3 subunit. The resulting cells, which have on the surface thereof increased numbers of Kv channels formed by the exogenogous Kvα subunits, are useful for testing the efficacy of compounds designed to alter current flow through the newly-expressed Kv channels such as, for example by measuring whole-cell currents using the conventional two microelectrode voltage-clamp technique.

The KChAP polynucleotides are also useful for producing KChAP constructs which are useful for producing KChAP protein or fragments thereof by recombinant techniques. Such constructs include, among others, vectors, such as a plasmid, phagemid, or viral vector, into which a sequence that encodes the KChAP protein has been inserted. Optionally, such constructs encode a fusion KChAP which includes an N-terminal or C-terminal peptide or tag that simplifies purification of the expressed recombinant product. Representative examples of such tags include sequences which encode a series of histidine residues, the Herpes simplex glycoprotein D, or glutathione S-transferase.

Polynucleotides encoding KChAP are also useful for designing hybridization probes for isolating and identifying cDNA clones and genomic clones encoding KChAP, or for identifying cells and tissues containing KChAP transcripts. Such hybridization techniques are known to those of skill in the art. Sequence of polynucleotides that encode human or rat KChAP are also useful for designing primers for polymerase chain reaction, a technique useful for obtaining large quantities of cDNA molecules that encode KChAP. Preferably, the primers comprise 18–30 nucleotides, more preferably 19–25 nucleotides. Preferably, the primers have a G+C content of 40% or greater.

Cloning the C Terminal Region of a cDNA that Encodes Rat KChAP

A cDNA encoding the C terminal region of rat KChAP was isolated using the Yeast Two-Hybrid Library Screen and a rat brain cDNA library in the GAL4 activation domain vector, pGAD10, obtained from Clontech. In this procedure the entire coding sequence of Kvβ1.2 (amino acids 1–408), which was used as bait for proteins that interact with Kvβ1.2, was subcloned in frame into the GAL4 DNA binding domain vector, pGBT9 from Clontech after PCR-mediated addition of a 5' EcoRi site and a 3' SalI site. The yeast Y190 strain (with two reporter genes, lacZ and HIS3) was cotransformed simultaneously with Kvβ1.2 pGBT9 and pGAD10 library DNA, and plated on synthetic medium lacking tryptophan (trp), leucine (leu), and histidine (his) plus 3-aminotriazole (25 mm) to prevent leaky transcription of the HIS3 gene. After incubation for 8 days at 30° C., His colonies were screened for β-galactosidase activity by a filter lift assay as outlined in Clontech protocols. Yeast DNA was isolated from colonies positive for both reporter genes using a phenol/glass-bead protocol (Clontech). Individual library plasmids were isolated after transformation of yeast DNA into chemically competent HB101 bacteria and growth on minimal medium lacking leucine. Individual pGAD10 recombinant plasmids were screened for interaction with Kvβ1.2 by repeating the yeast two-hybrid assay in Y190 cells. One plasmid, designated herein as the "KChAP-Y plasmid", activated transcription of the reporter genes in cells co-transformed simultaneously with Kvβ1.2 pGBT9, but did not activate transcription in control cells transformed with the KChAP-Y plasmid alone.

KChAP-Y plasmid cDNA was sequenced, and found to comprise a 1.78 kb insert encoding an open reading frame of 264 amino acids and 980 base pairs of 3' untranslated sequence including the poly (A+) tail. This insert or fragment is designated herein as "KChAP-Y".

Cloning of a Full-Length cDNA Encoding Rat KChAP

A polynucleotide encoding KChAP-Y was used as a probe to obtain a full-length cDNA encoding KChAP. In this procedure, the $^{32}$P labeled KChAP-Y insert was used to screen a rat brain cDNA library in λgt10 from Clontech. One of the hybridizing clones contained an insert of 3.2 kb with a single open reading frame encoding a protein of 574 amino acids. The start methionine was identified as the first ATG downstream from three in frame stop codons.

The full length cDNA encoding KChAP, designated herein as the "KChAP gene" is shown schematically in FIG. 1. The sequence of the KChAP gene is shown in FIG. 2 and set forth in SEQ ID NO: 1. Hydropathy analysis showed no putative membrane spanning regions in KChAP. The open reading frame of the KChAP gene predicts a protein of 574 amino acids and having the sequence shown in FIG. 2, SEQ ID NO: 2. The open reading frame of the KChAP gene is flanked by 219 base pairs of untranslated sequence on the 5' end, and 980 base pairs of 3' untranslated sequence. The 980 base pair sequence as indicated by the thin lines in FIG. 1. The Kvα/Kβ binding domain on the KChAP gene has been localized to the region which encodes amino acids W310 through L407. The Kvα/Kvβ binding domain has the amino acid sequence set forth in SEQ ID NO: 5. KChAP-Y extends from amino acid W310 of the full-length KChAP protein through the poly A tail at the 3' end.

In Vitro Transcription and Translation of the KChAP Gene

Full-length KChAP cDNA was removed from pGBT9 with EcoRI and SalI and subcloned into a pCR3 vector which was modified to allow the cloning of EcoRI/SalI fragments in frame behind a c-myc tag. The KChAP fragment for subcloning was prepared by PCR to contain only a consensus Kozak sequence at the 5' end and a poly (A+) tail just past the stop codon at the 3' end to eliminate most of the 5' and 3' untranslated sequences in the expression construct. KChAP cRNA was prepared using the T7 mMESSAGE mMACHINE kit (Ambion) following linearization of the construct with NotI. cRNA for c-myc-KChAP was translated in vitro in a rabbit reticulocyte lysate to provide the fusion protein c-myc-KChAP.

Cloning of a Full-Length cDNA Encoding Human KChAP

Reverse transcriptase and polymerase chain reaction (RT-PCR) techniques were used to clone a cDNA encoding human KChAP. The template was human brain poly A+ RNA from Clonetech. The reverse transcription reaction mixture was incubated for 1 hour at 42° C., and then heat inactivated.

PCR amplification was performed using the sense primer 5'ATGAAGATCAAAGAGCTTTACCGACG 3', SEQ ID NO: 12 and the antisense primer 5'TCAGTCCAGG-GAAATCATGACCG 3', SEQ ID NO: 13, which flank the start methionine and stop codon, respectively. The following reagent concentrations were used for amplification: 5% DMSO, 0.2 mM of each dNTP, 0.2 pmole/µl of each oligomeric primer, Clonetech's Advantage cDNA polymerase mix and buffer. The cycling protocol was as follows: one cycle at 94° C. for 2 minutes; 35 cycles at 94° C. for 15 seconds, 50° C. for 15 seconds, and 72° C. for 30 seconds; and one cycle at 72° C. for 10 minutes.

The PCR product was gel-purified using Qiaquick Gel Extraction Kit from Qiagen, sub-cloned into PCRII from Invitrogen and sequenced using Sequenase from U.S. Biochemicals. The nucleotide sequence of the open reading frame, SEQ ID NO: 3, and the predicted amino acid sequence, SEQ ID NO: 4, encoded thereby are shown in FIG. 3.

Increasing the Number of Kv2.1, 2.2, 1.3 and 4.3 Channels in Host Cells

A. Materials

Human Gu binding protein cDNA encoding the peptide spanning amino acids M49 to D645 was obtained by RT-PCR from human brain poly A+ RNA and subcloned into pCRII (Invitrogen) for transcription. A Kozak sequence was included in the 5' oligo to facilitate translation in oocytes. cRNAs for Kv1α-subunits were prepared as described in Majumder et al, (1995), FEBS Letts, 377, 383–389, and Wang et al. (1996), J. Bio. Chem., 271, 28311–28317. cRNA encoding Kv2.1ΔN (in which the N-terminal 139 amino acids had been deleted) prepared was as described in Van- Dongen et al, (1990), Neuron 5, 433–443. HERG cDNA was obtained from Dr. M. Keating. Kv2.2 was obtained from Drs. S. Snyder and J. Trimmer. Rat Kv2.1 in pBluescript was linearized with NotI and cRNA was prepared with T7 polymerase. cRNA concentrations were estimated on denaturing agarose gels stained with ethidium bromide by comparison with RNA standards. cRNAs were mixed and injected into Xenopus oocytes as described in Majumder et al, (1995).

B. Methods

Xenopus oocytes were co-injected with cRNA molecules encoding human KChAP protein or rat KChAP protein and with cRNA molecules encoding one of the following Kvα subunits: Kv1.2, Kv1.5, Kv3.1, Kv2.1, Kv2.2 and Kv4.3, or with cRNA molecules encoding Kir 2.2, HERG, and Kv2.1ΔN. As a control, Xenopus oocytes were injected with cRNA molecules encoding the α-subunits alone. For comparison Xenopus oocytes were co-injected with cRNA molecules encoding human Gu binding protein and the α-subunits.

Whole oocyte currents were measured either two days after co-injection of c-myc-KChAP cRNA and cRNAs encoding Kv4.3, Kv1.2, Kv3.1, Kir 2.2, or aKv2.1ΔN, or five days post-injection from oocytes injected with cRNAs encoding Kv2.1, Kv2.2, Kv1.5 or HERG plus c-myc-KChAP cRNA. Bath solution contained (in mmol/liter): 5 KOH, 100 NaOH, 0.5 $CaCl_2$, 2 $MgCl_2$, 100 MES, and 10 HEPES (pH 7.4). Solution containing 50 $K^+$ was prepared by replacing an equivalent concentration of $Na^+$. Electrodes were filled with 3 M KCl and had a resistance of 0.3–0.6 MΩ. All recordings were made at room temperature. Linear leakage and capacity transient currents were subtracted (P/4 prepulse protocol) unless specified and data were low pass filtered at 1 kHz. pClamp software (Axon Instruments) was used for generation of the voltage-pulse protocols and data acquisition. Means±S.E.M. were calculated and were considered to be significantly different when $P<0.05$. Comparisons among multiple groups of oocytes were performed by one-way ANOVA test and Student-Newman-Keuls post-hoc test (SKN test).

For Kv1.2, Kv1.5, Kv2.1, Kv2.1ΔN, Kv2.2 Kv3.1 and Kv4.3 channels holding potential was –80 mV. Peak (Kv4.3) or steady state (other channels) currents were measured at a test potential of +70 mV (5 or 50 K+ in the bath). Kir 2.2 and HERG currents were recorded with 50 K+ in the bath at test potential to –100 mv with a pre-pulse to +20 mV.

The results indicated that co-injection of oocytes with cRNA encoding KChAP and encoding either Kv2.1 α subunit, or Kv2.2 α subunit, or Kv4.3 α subunit significantly increased the amplitude of Kv2.1, Kv2.2, and Kv4.3 currents as compared to oocytes injected with these respective α-subunits alone. No change was observed in the currents of control oocytes or oocytes coinjected with cRNA encoding KChAP and cRNA encoding either Kv1.2 α subunit, or Kv1.5 α subunit, or Kv3.1α subunit. The results also indicated that KChAP did not alter the kinetics or gating of Kv2.1, Kv2.2, or Kv4.3 channels.

Several hours after recording, the oocytes injected with cRNA molecules encoding KChAP and Kv2.2 α subunit were fixed in 4% paraformaldehyde. 50 μm vibrotome sections were cut, and incubated for 2 hours in 1% BSA/PBS to block nonspecific binding sites. The sections were incubated at 4° C. overnight in primary antibodies, that is an anti-Kv2.1 α subunit, rabbit polyclonal antibody, from Upstate Biotechnology, Inc.; and anti-c-myc, a mouse monoclonal antibody, from Boehringer Mannheim, Inc. The sections were washed, and incubated for 2 hours at room temperature in secondary antibodies, FITC-conjugated anti-rabbit for Kv2.1 and TRITC-conjugated anti-mouse for c-myc. Sections were examined with an Olympus BH-2 microscope for the appearance of fluorescence.

The FITC fluorescence, which indicates the amount of Kv2.1 α subunit, was much brighter at the oocyte surface in eggs expressing both Kv2.1 and KChAP as compared to eggs expressing the Kv2.1 α subunit alone. Thus, co-injection cRNA molecules encoding KChAP with cRNA encoding either Kv2.1, Kv2.2, or Kv4.3 α subunits increases the number of functional Kv2.1, Kv2.2 and Kv4.3 channels on the plasma membrane of cells as compared to cells injected with cRNA molecules encoding the Kvα subunits alone. By increasing the number of functional Kv2.1, Kv2.2 and Kv4.3 channels on the surface of a host cell, one can more readily study the channels and more easily observe the effect of pharmaceutical agents on such channels.

Interaction of KChAP with Kvα and Kvβ Subunits

The interaction of KChAP with particular Kvα and β subunits was examined using an indirect and direct procedure.

(a) Indirect Procedure for Monitoring Interaction of KChAP with Kvα and Kvβ Subunits In the indirect procedure, the yeast Matchmaker Two-Hybrid System Clontech and cDNA molecules encoding KChAP and KChAP-Y were used. The binding specificity between full length KChAP or KChAP-Y and the following Kvα, Kvβ and other K+ channel subunit fragments were determined: Kvβ1.2 (amino acids 1–408), Kvβ1.2-N terminus (amino acids 1–79), Kvβ1C (carboxyl terminal 329 amino acids of the Kvβ1 subfamily), Kvβ2 (amino acids 1–367); Kv1.1-N terminus (amino acids 1–168), Kv1.2 N-terminus (amino acids 1–124), Kv1.4 N-terminus (amino acids 1–305), Kv1.4 C-terminus (amino acids 562–654), Kv1.5 N-terminus (amino acids 1–248), Kv2.1 N-terminus (amino acids 1–168), Kv2.2 N-terminus (amino acids 1–185), Kv6.1 N-terminus (amino acids 1–209), Kir2.2 N-terminus (amino acids 1–86), and HERG N-terminus (amino acids 1–396). The ability of human Gu-binding protein (GBP) to bind to these fragments was also determined.

Protein-protein interactions were tested by co-transformation of the yeast host strain Y190 with a pGAD10 plasmid containing inserts encoding KChAP-Y, KChAP or GBP with a pGBT9 plasmid containing an insert encoding one of the K+ channel protein fragments. pGBT9 is a GAL4 DNA binding domain [BD] vector. Co-transformants were plated on medium lacking trp and leu and grown for 2.5 days at 30° C. Yeast colonies were lifted to paper filters and assayed for β-galactosidase activity. Appearance of blue color within 8 hours was scored as a positive interaction between the proteins encoded by the two plasmids.

KChAP and KChAP-Y interacted with the fragments in a similar manner. KChAP interacted with the N-terminus of Kvα1 subunits and the Kvα2 subunits. KChAP also associated with the C terminus of Kvβ1 and Kvβ2 with no apparent interaction with the Kvβ1.2 N-terminus. No binding was observed to the C-terminus of Kv1.4, nor to the N-termini of either HERG, Kir2.2, or Kv6.1. KChAP-Y interacted with the N-termini of Kv1.1, Kv1.2, Kv1.4, and Kv1.5. No interaction was evident between the Kv1.4 C-terminus and KChAP-Y. KChAP-Y also interacted with the N-termini of Kv2.1 and Kv2.2, but not with the N-terminus of the electrically silent Kv2 partner, Kv6.1. Further specificity for a subset of Kv channels was apparent from the lack of interaction with the N-terminus of the inward rectifier K⁺ channel, Kir2.2, and the N-terminus of the delayed rectifier K⁺ channel, HERG. Thus, KChAP-Y both interact with the C-terminus of Kvβ subunits as well as the N-termini of Kv1 and Kv2 α-subunits.

The minimal KChAP sequence sufficient for Kvα and Kvβ binding was determined by expressing fragments of KChAP in yeast two-hybrid assays with the Kv fragments. The results indicated that the Kvα and Kvβ binding domain of KChAP is localized to a region between amino acids W310 and L407. Gu binding protein did not interact with any of the fragments. Thus, although KChAP shares 50% homology with GBP, interaction with Kvβ and Kvα subunits appears to be a unique feature of KChAP.

(b) Direct Procedure for Monitoring Interaction of KChAP and Kvα and Kvβ Subunits The direct procedure involved immunoprecipitation of protein complexes produced by in vitro translation of cRNA for c-myc-KChAP and cRNA for the α-subunit Kv2.1. These cRNA molecules were translated in vitro either separately to produce individual proteins or together to produce complexes in rabbit reticulocyte lysates in the presence of $^{35}$S-methionine using the Retic Lysate IVT kit (Ambion). For immunoprecipitation (IP), 10 μl aliquots of each translation mixture were diluted into 1 ml IP buffer (1% Triton X-100, 150 mM NaCl, 50 mM Tris pH 7.5, 1 mM EDTA). To monitor the ability of the two proteins to associate after translation, 10 μl aliquots of individual translates of Kv2.1 and c-myc-KChAP were mixed in 1 ml IP buffer prior to addition of antibody. IP was performed with two primary antibodies: anti-Kv2.1 polyclonal (1:100 dilution; Upstate Biotechnology, Inc.) or anti-c-myc monoclonal (1:400; Boehringer Mannheim). After addition of the primary antibody, the reactions were mixed gently overnight at 4° C. Immune complexes were collected on magnetic beads coupled to either anti-rabbit or anti-mouse secondary antibodies (Dynal, Inc.). After four washes in IP buffer, bound protein was eluted by boiling in SDS sample buffer, and analyzed on 10% polyacrylamide/SDS gels. The gel was fixed, soaked in Amplify (Amersham), and radiolabeled protein detected by fluorography.

The anti-Kv2.1 antibody immuno-precipitated complexes of Kv2.1 and c-myc-KChAP from translation reactions in which the two proteins were co-translated. The formation of a complex between KChAP and Kv2.1 shows a direct interaction between the two proteins. No complexes of Kv2.1 and c-myc-KChAP were detected in samples in which the Kv2.1 and c-myc-KChAP were translated separately and mixed together before the addition of primary antibody This result suggests that the association of KChAP with Kv2.1 occurs co-translationally since the mature proteins added after translation did not co-immunoprecipitate.

Altering the Effect of Kvβ1-C on Kv1.5 Currents

Xenopus oocytes were co-injected with cRNA molecules encoding KChAP and cRNA molecules encoding Kv1.5 α subunit and Kvβ1-C. Kvβ1-C is known to interact with the Kv1.5 α subunit within the cell and to decrease Kv1.5 currents. As a control, Xenopus oocytes were injected with cRNA encoding the Kv1.5 α subunit alone or with cRNA molecules encoding Kv1.5 α subunit and Kvβ1-C. Whole cell-currents were measured five days after injection. Holding potential was −80 mV and pulses were from −70 mV to +70 mV in 10 mV steps with 5 mM K⁺ in the bath solution.

Co-injection into cells of cRNA encoding KChAP and cRNA's encoding Kv1.5 α subunit and Kvβ1-C blocked the effect of Kvβ1-C on Kv1.5 currents.

Presence of KChAP in the Nucleus

Examination of the COS-7 cells and mouse L cells transfected with c-myc-KChAP cDNA and stained with FITC-labeled c-myc antibodies indicate that at least a portion of KChAP is located in the nucleus.

KChAP Expression in Rat Tissues

A $^{32}$P-labeled riboprobe was prepared from a fragment of rat KChAP cDNA encoding the C-terminal 167 amino acids. This is the region of the KChAP protein which differs most from GBP. The riboprobe was used to probe A rat Multiple Tissue Northern blot (2 μg poly A⁺ RNA per lane) from Clontech. The hybridization was done overnight in NorthernMax hybridization buffer from Ambion at 68° C. The blot was washed with in 0.1×SSC/0.1% SDS at 70° C. Autoradiography was performed for 5 hours at −70° C. with Kodak Biomax MS film and intensifying screen. The results indicated that KChAP transcripts are most abundant in heart, brain, skeletal muscle, lung, spleen and kidney.

Interaction of KChAP with the Tumor Suppresser Product p53

The interaction of KChAP with the tumor suppresser gene product p53 was examined using the yeast two-hybrid system. The results indicated that p53 binds to the Kvβ/Kvα binding domain of KChAP. Co-injection into Xenopus oocytes of cRNA molecules that encode p53 along with cRNA molecules that encode KChAP and the Kv2.1 α subunit suppressed the stimulatory effect of KChAP on formation of Kv2.1 channels.

Testing the Effects of a Compound on Current Flow through Kv Channels

In order to test the stimulatory or inhibitory effect of a compound, particularly a pharmacological agent, on the flow of current through Kv channels, it is desirable to have a model system comprising a population of cells that have increased numbers of Kv channels on their cellular plasma membranes. Such model system is especially suitable for measuring small changes in current flow. Such model systems are prepared by co-injecting into host cells cRNA molecules encoding KChAP and cRNA molecules encoding a Kvα subunit. The encoding regions for KChAP and for the Kvα subunit may both be on a single cRNA molecule, or the encoding regions for KChAP and for the Kvα subunit may be on separate cRNA molecules. Preferably, the Kvα subunit is an exogenous Kvα subunit, i.e., the Kvα subunit is not normally expressed in the cell. Such model systems are especially useful for monitoring the effect of a compound on a particular Kv channel, i.e., the Kv channel formed by assembly of a plurality of the exogenous Kvα subunits. Thereafter, the cells are cultured for a time and under conditions which permit transformation of the host cells, i.e., expression of the co-injected cRNA molecules and assembly of Kv channels comprising the corresponding Kvα subunits.

The compound, which has been dissolved in a suitable carrier, is added to the culture medium of a test population of transformed host cells. Preferably, a plurality of concentrations of the compound are added to a corresponding plurality of test populations. The compound is also added to the culture medium of a control population of cells that have not been tranformed, i.e., cRNA molecules encoding KChaP and the Kvα subunit are not injected into the cells. Thereafter, whole cell currents are measured using conventional techniques, such as for example, using a two microelectrode voltage-clamp technique and the gigaseal patch clamp technique. A difference between whole cell currents in the control population and the test populations is indicative of a stimulatory or inhibitory effect of the compound on the Kv channels formed by the exogenous Kvα subunit. Such measurements are also used to determine the effective compound dosage.

While the invention has been described to some degree of particularity, various adaptations and modifications can be made without departing from the scope of the invention as defined in the appended claims.

What is claimed is:

1. A method for increasing the number of Kv channels formed by a Kvα subunit on the plasma membrane of a host cell, comprising the steps of:
    (a) providing a cRNA molecule comprising a nucleotide sequence encoding a KChAP protein or variant thereof, wherein said KChAP protein or variant thereof comprises an amino acid sequence that is at least 95% identical to SEQ ID NO:2 or SEQ ID NO: 4, and binds to said Kvα subunit;
    (b) providing a cRNA molecule comprising a nucleotide sequence encoding said Kvα subunit; wherein the nucleotide sequence encoding said KChAP protein or variant thereof and the nucleotide sequence encoding said Kvα subunit may be on the same or different cRNA molecules;
    (c) introducing the cRNA molecule encoding said KChAP protein or variant thereof and the cRNA encoding said Kvα subunit into the host cell; and
    (d) co-expressing the KChAP protein or the variant thereof and the Kvα subunit, thereby increasing the number of Kv channels formed by the Kvα subunit on the plasma membrane of the host cell.

2. A method for increasing the number of Kv channels formed by a Kvα subunit on the plasma membrane of a host cell, comprising the steps of:

(a) transfecting the host cell with a polynucleotide comprising a nucleotide sequence encoding a KChAP protein or a variant thereof, wherein said KChAP protein or variant thereof comprises an amino acid sequence which is at least 95% identical to SEQ ID NO:2 or SEQ ID NO: 4, and binds to the Kvα subunit;

(b) transfecting the host cell with a polynucleotide comprising a nucleotide sequence encoding said Kvα subunit; and (c) co-expressing the KChAP protein and the Kvα subunit, thereby increasing the number of Kv channels formed by the Kvα subunit on the plasma membrane of the host cell.

3. The method of claim 1 wherein the Kvα subunit is Kv2.1, Kv2.2, Kv1.3, Kv 4.3, or combinations thereof.

4. The method of claim 2 wherein the Kvα subunit is Kv2.1, Kv2.2, Kv1.3, Kv 4.3, or combinations thereof.

5. The method of claim 1 wherein said cRNA comprises a sequence which encodes SEQ ID NO. 2.

6. The method of claim 1 wherein said cRNA comprises a sequence which encodes SEQ ID NO. 4.

7. The method of claim 1 wherein said cRNA comprises a sequence which encodes SEQ ID NO. 6.

8. The method of claim 2 wherein said polynucleotide comprises a sequence which encodes SEQ ID NO. 2.

9. The method of claim 2 wherein said polynucleotide comprises a sequence which encodes SEQ ID NO. 4.

10. The method of claim 2 wherein said polynucleotide comprises a sequence which encodes SEQ ID NO. 6.

* * * * *

UNITED STATES PATENT AND TRADEMARK OFFICE
CERTIFICATE OF CORRECTION

PATENT NO. : 6,391,561 B1
DATED : May 21, 2002
INVENTOR(S) : Arthur M. Brown, Barbara A. Wible and Qing Yang It is certified that error appears in the above-identified patent and that said Letters Patent is hereby corrected as shown below:

<u>Column 2,</u>
Line 36, after "NO:" please delete "2" and insert -- 4 --.

Signed and Sealed this

Twenty-second Day of October, 2002

Attest:

Attesting Officer

JAMES E. ROGAN
*Director of the United States Patent and Trademark Office*

SEQUENCE LISTING

<160> NUMBER OF SEQ ID NOS: 13

<210> SEQ ID NO 1
<211> LENGTH: 1725
<212> TYPE: DNA
<213> ORGANISM: Rattus norvegicus
<220> FEATURE:
<221> NAME/KEY: CDS
<222> LOCATION: (1)..(1725)

<400> SEQUENCE: 1

```
atg aag atc aaa gaa ctt tac cgc agg cgc ttt ccc cgg aag acc ctg      48
Met Lys Ile Lys Glu Leu Tyr Arg Arg Arg Phe Pro Arg Lys Thr Leu
1               5                   10                  15 ggg cct tcc gat ctc tct ttg ctc tct ttg ccc cct ggc acc tct cct      96
Gly Pro Ser Asp Leu Ser Leu Leu Ser Leu Pro Pro Gly Thr Ser Pro
            20                  25                  30 gta ggc tcc ccc agc ccc ctt gct tcc att cct ccc acc ctc ctg acc     144
Val Gly Ser Pro Ser Pro Leu Ala Ser Ile Pro Pro Thr Leu Leu Thr
        35                  40                  45 cct ggc acc ttg ctg ggc cct aag cgt gag gtg gac atg cac cct cct     192
Pro Gly Thr Leu Leu Gly Pro Lys Arg Glu Val Asp Met His Pro Pro
    50                  55                  60 ctg ccc cag cct gtg cac cct gac gtc acc atg aaa cca ctg ccc ttc     240
Leu Pro Gln Pro Val His Pro Asp Val Thr Met Lys Pro Leu Pro Phe
65                  70                  75                  80 tac gaa gtc tac gga gag ctc atc cgg ccg acc acc ctt gcg tcc acc     288
Tyr Glu Val Tyr Gly Glu Leu Ile Arg Pro Thr Thr Leu Ala Ser Thr
                85                  90                  95 tcc agt cag agg ttt gag gaa gcc cac ttt acc ttt gca ctc act ccc     336
Ser Ser Gln Arg Phe Glu Glu Ala His Phe Thr Phe Ala Leu Thr Pro
            100                 105                 110 cag cag ctg cag cag att ctc aca tcc agg gag gtt ctg cca gga gcc     384
Gln Gln Leu Gln Gln Ile Leu Thr Ser Arg Glu Val Leu Pro Gly Ala
        115                 120                 125 aag tgc gat tat acc ata caa gtg cag ctc agg ttc tgt ctc tgt gag     432
Lys Cys Asp Tyr Thr Ile Gln Val Gln Leu Arg Phe Cys Leu Cys Glu
    130                 135                 140 acc agc tgc ccc cag gag gac tat ttc ccc cct aac ctc ttt gtc aag     480
Thr Ser Cys Pro Gln Glu Asp Tyr Phe Pro Pro Asn Leu Phe Val Lys
145                 150                 155                 160 gtt aat ggg aaa ctc tgc ccc ctg ccg ggt tac ctc cct cca acc aag     528
Val Asn Gly Lys Leu Cys Pro Leu Pro Gly Tyr Leu Pro Pro Thr Lys
                165                 170                 175 aat gga gct gag ccc aag agg cct agt cgt cca atc aac atc aca ccc     576
Asn Gly Ala Glu Pro Lys Arg Pro Ser Arg Pro Ile Asn Ile Thr Pro
            180                 185                 190 ctg gct cgt ctc tca gcc act gtt ccc aac acc ata gtg gtt aac tgg     624
Leu Ala Arg Leu Ser Ala Thr Val Pro Asn Thr Ile Val Val Asn Trp
        195                 200                 205 tca tct gag ttt gga cgg aat tac tcc ttg tct gtg tac ctg gtg agg     672
Ser Ser Glu Phe Gly Arg Asn Tyr Ser Leu Ser Val Tyr Leu Val Arg
    210                 215                 220 cag ttg act gca ggg acc ctg cta caa aag ctc aga gcc aag ggt atc     720
Gln Leu Thr Ala Gly Thr Leu Leu Gln Lys Leu Arg Ala Lys Gly Ile
225                 230                 235                 240
```

-continued

```
cgg aat cca gac cat tcc cga gca ctg atc aag gag aaa ttg act gct        768
Arg Asn Pro Asp His Ser Arg Ala Leu Ile Lys Glu Lys Leu Thr Ala
            245                 250                 255 gac ccc gac agt gaa gtg gct act aca agt ctc cgg gtg tca ctc atg        816
Asp Pro Asp Ser Glu Val Ala Thr Thr Ser Leu Arg Val Ser Leu Met
        260                 265                 270 tgc ccg ctg ggg aag atg cgc ctg act gtc cca tgc cgc gct ctc acc        864
Cys Pro Leu Gly Lys Met Arg Leu Thr Val Pro Cys Arg Ala Leu Thr
    275                 280                 285 tgt gcc cac ctg cag agt ttc gat gct gcc ctt tat cta cag atg aat        912
Cys Ala His Leu Gln Ser Phe Asp Ala Ala Leu Tyr Leu Gln Met Asn
290                 295                 300 gag aaa aag cca aca tgg acg tgc cct gtg tgt gac aag aag gct ccc        960
Glu Lys Lys Pro Thr Trp Thr Cys Pro Val Cys Asp Lys Lys Ala Pro
305                 310                 315                 320 tat gag tca ctg att att gat ggt tta ttc atg gaa att ctt aat tcc       1008
Tyr Glu Ser Leu Ile Ile Asp Gly Leu Phe Met Glu Ile Leu Asn Ser
                325                 330                 335 tgt tcg gat tgt gat gag atc cag ttc atg gaa gat gga tcc tgg tgt       1056
Cys Ser Asp Cys Asp Glu Ile Gln Phe Met Glu Asp Gly Ser Trp Cys
            340                 345                 350 cca atg aaa ccc aag aag gag gca tcc gag gtt tgc ccc cca cca ggg       1104
Pro Met Lys Pro Lys Lys Glu Ala Ser Glu Val Cys Pro Pro Pro Gly
        355                 360                 365 tat ggg ctg gat ggt ctc cag tat agc cca gtc cag gag gga aat cag       1152
Tyr Gly Leu Asp Gly Leu Gln Tyr Ser Pro Val Gln Glu Gly Asn Gln
    370                 375                 380 tca gag aat aag aag agg gtt gaa gtc att gac ttg aca atc gaa agc       1200
Ser Glu Asn Lys Lys Arg Val Glu Val Ile Asp Leu Thr Ile Glu Ser
385                 390                 395                 400 tca tca gat gag gaa gat ctg ccc ccc acc aag aag cac tgc cct gtt       1248
Ser Ser Asp Glu Glu Asp Leu Pro Pro Thr Lys Lys His Cys Pro Val
                405                 410                 415 acc tcg gct gcc att cca gcc ctt cct gga agc aaa gga gcc ctg acc       1296
Thr Ser Ala Ala Ile Pro Ala Leu Pro Gly Ser Lys Gly Ala Leu Thr
            420                 425                 430 tct ggt cac cag ccg tct tcg gtg ctg cgg agc cct gca atg ggt aca       1344
Ser Gly His Gln Pro Ser Ser Val Leu Arg Ser Pro Ala Met Gly Thr
        435                 440                 445 ctg ggc agt gat ttc ctg tct agt ctc cca cta cat gag tac cca cct       1392
Leu Gly Ser Asp Phe Leu Ser Ser Leu Pro Leu His Glu Tyr Pro Pro
    450                 455                 460 gcc ttc ccg ctg ggg gct gac atc caa ggt tta gat tta ttt tct ttc       1440
Ala Phe Pro Leu Gly Ala Asp Ile Gln Gly Leu Asp Leu Phe Ser Phe
465                 470                 475                 480 ctt cag act gag agt cag cac tac agc cct tca gtt atc act tca cta       1488
Leu Gln Thr Glu Ser Gln His Tyr Ser Pro Ser Val Ile Thr Ser Leu
                485                 490                 495 gat gag cag gac acc ctt ggc cac ttc ttc caa ttc cgg gga acc cct       1536
Asp Glu Gln Asp Thr Leu Gly His Phe Phe Gln Phe Arg Gly Thr Pro
            500                 505                 510 ccc cac ttc ctg ggc cca ctg gcc ccc aca ttg ggg agc tct cac cgc       1584
Pro His Phe Leu Gly Pro Leu Ala Pro Thr Leu Gly Ser Ser His Arg
        515                 520                 525 agc gcc act cca gca ccc gct cct ggc cgt gtc agc agc att gtg gct       1632
Ser Ala Thr Pro Ala Pro Ala Pro Gly Arg Val Ser Ser Ile Val Ala
    530                 535                 540 cct ggg agt tcc ttg agg gaa ggg cat gga gga ccc ctg cct tcc ggt       1680
Pro Gly Ser Ser Leu Arg Glu Gly His Gly Gly Pro Leu Pro Ser Gly
545                 550                 555                 560
```

```
ccc tct ttg act ggc tgt cgg tca gac gtc att tcc ttg gac tga        1725
Pro Ser Leu Thr Gly Cys Arg Ser Asp Val Ile Ser Leu Asp
            565                 570
```

<210> SEQ ID NO 2
<211> LENGTH: 574
<212> TYPE: PRT
<213> ORGANISM: Rattus norvegicus

<400> SEQUENCE: 2

```
Met Lys Ile Lys Glu Leu Tyr Arg Arg Phe Pro Arg Lys Thr Leu
1               5                   10                  15

Gly Pro Ser Asp Leu Ser Leu Leu Ser Leu Pro Pro Gly Thr Ser Pro
                20                  25                  30

Val Gly Ser Pro Ser Pro Leu Ala Ser Ile Pro Pro Thr Leu Leu Thr
            35                  40                  45

Pro Gly Thr Leu Leu Gly Pro Lys Arg Glu Val Asp Met His Pro Pro
        50                  55                  60

Leu Pro Gln Pro Val His Pro Asp Val Thr Met Lys Pro Leu Pro Phe
65                  70                  75                  80

Tyr Glu Val Tyr Gly Glu Leu Ile Arg Pro Thr Thr Leu Ala Ser Thr
                85                  90                  95

Ser Ser Gln Arg Phe Glu Glu Ala His Phe Thr Phe Ala Leu Thr Pro
                100                 105                 110

Gln Gln Leu Gln Gln Ile Leu Thr Ser Arg Glu Val Leu Pro Gly Ala
            115                 120                 125

Lys Cys Asp Tyr Thr Ile Gln Val Gln Leu Arg Phe Cys Leu Cys Glu
130                 135                 140

Thr Ser Cys Pro Gln Glu Asp Tyr Phe Pro Pro Asn Leu Phe Val Lys
145                 150                 155                 160

Val Asn Gly Lys Leu Cys Pro Leu Pro Gly Tyr Leu Pro Pro Thr Lys
                165                 170                 175

Asn Gly Ala Glu Pro Lys Arg Pro Ser Arg Pro Ile Asn Ile Thr Pro
            180                 185                 190

Leu Ala Arg Leu Ser Ala Thr Val Pro Asn Thr Ile Val Val Asn Trp
        195                 200                 205

Ser Ser Glu Phe Gly Arg Asn Tyr Ser Leu Ser Val Tyr Leu Val Arg
210                 215                 220

Gln Leu Thr Ala Gly Thr Leu Leu Gln Lys Leu Arg Ala Lys Gly Ile
225                 230                 235                 240

Arg Asn Pro Asp His Ser Arg Ala Leu Ile Lys Glu Lys Leu Thr Ala
                245                 250                 255

Asp Pro Asp Ser Glu Val Ala Thr Thr Ser Leu Arg Val Ser Leu Met
            260                 265                 270

Cys Pro Leu Gly Lys Met Arg Leu Thr Val Pro Cys Arg Ala Leu Thr
        275                 280                 285

Cys Ala His Leu Gln Ser Phe Asp Ala Ala Leu Tyr Leu Gln Met Asn
        290                 295                 300

Glu Lys Lys Pro Thr Trp Thr Cys Pro Val Cys Asp Lys Lys Ala Pro
305                 310                 315                 320

Tyr Glu Ser Leu Ile Ile Asp Gly Leu Phe Met Glu Ile Leu Asn Ser
                325                 330                 335

Cys Ser Asp Cys Asp Glu Ile Gln Phe Met Glu Asp Gly Ser Trp Cys
            340                 345                 350
```

-continued

```
Pro Met Lys Pro Lys Lys Glu Ala Ser Glu Val Cys Pro Pro Gly
    355                 360                 365

Tyr Gly Leu Asp Gly Leu Gln Tyr Ser Pro Val Gln Glu Gly Asn Gln
370                 375                 380

Ser Glu Asn Lys Lys Arg Val Glu Val Ile Asp Leu Thr Ile Glu Ser
385                 390                 395                 400

Ser Ser Asp Glu Glu Asp Leu Pro Pro Thr Lys Lys His Cys Pro Val
                405                 410                 415

Thr Ser Ala Ala Ile Pro Ala Leu Pro Gly Ser Lys Gly Ala Leu Thr
            420                 425                 430

Ser Gly His Gln Pro Ser Ser Val Leu Arg Ser Pro Ala Met Gly Thr
        435                 440                 445

Leu Gly Ser Asp Phe Leu Ser Ser Leu Pro Leu His Glu Tyr Pro Pro
    450                 455                 460

Ala Phe Pro Leu Gly Ala Asp Ile Gln Gly Leu Asp Leu Phe Ser Phe
465                 470                 475                 480

Leu Gln Thr Glu Ser Gln His Tyr Ser Pro Ser Val Ile Thr Ser Leu
                485                 490                 495

Asp Glu Gln Asp Thr Leu Gly His Phe Phe Gln Phe Arg Gly Thr Pro
                500                 505                 510

Pro His Phe Leu Gly Pro Leu Ala Pro Thr Leu Gly Ser Ser His Arg
            515                 520                 525

Ser Ala Thr Pro Ala Pro Ala Pro Gly Arg Val Ser Ser Ile Val Ala
        530                 535                 540

Pro Gly Ser Ser Leu Arg Glu Gly His Gly Gly Pro Leu Pro Ser Gly
545                 550                 555                 560

Pro Ser Leu Thr Gly Cys Arg Ser Asp Val Ile Ser Leu Asp
                565                 570
```

<210> SEQ ID NO 3
<211> LENGTH: 1725
<212> TYPE: DNA
<213> ORGANISM: Homo sapiens
<220> FEATURE:
<221> NAME/KEY: CDS
<222> LOCATION: (1)..(1725)

<400> SEQUENCE: 3

```
atg aag atc aaa gag ctt tac cga cga cgc ttt ccc cgg aag acc ctg      48
Met Lys Ile Lys Glu Leu Tyr Arg Arg Arg Phe Pro Arg Lys Thr Leu
1               5                   10                  15 ggg ccc tct gat ctc tcc ctt ctc tct ttg ccc cct ggc acc tct cct      96
Gly Pro Ser Asp Leu Ser Leu Leu Ser Leu Pro Pro Gly Thr Ser Pro
            20                  25                  30 gta ggc tcc cct ggt cct cta gct ccc att ccc cca acg ctg ttg gcc    144
Val Gly Ser Pro Gly Pro Leu Ala Pro Ile Pro Pro Thr Leu Leu Ala
        35                  40                  45 cct ggc acc ctg ctg ggc ccc aag cgt gag gtg gac atg cac ccc cct    192
Pro Gly Thr Leu Leu Gly Pro Lys Arg Glu Val Asp Met His Pro Pro
    50                  55                  60 ctg ccc cag cct gtg cac cct gat gtc acc atg aaa cca ttg ccc ttc    240
Leu Pro Gln Pro Val His Pro Asp Val Thr Met Lys Pro Leu Pro Phe
65                  70                  75                  80 tat gaa gtc tat ggg gag ctc atc cgg ccc acc acc ctt gca tcc act    288
Tyr Glu Val Tyr Gly Glu Leu Ile Arg Pro Thr Thr Leu Ala Ser Thr
                85                  90                  95 tct agc cag cgg ttt gag gaa gcg cac ttt acc ttt gcc ctc aca ccc    336
Ser Ser Gln Arg Phe Glu Glu Ala His Phe Thr Phe Ala Leu Thr Pro
```

-continued

| | | |
|---|---|---|
| cag caa gtg cag cag att ctt aca tcc aga gag gtt ctg cca gga gcc<br>Gln Gln Val Gln Gln Ile Leu Thr Ser Arg Glu Val Leu Pro Gly Ala<br>               115                          120                      125 | 384 |
| aaa tgt gat tat acc ata cag gtg cag cta agg ttc tgt ctc tgt gag<br>Lys Cys Asp Tyr Thr Ile Gln Val Gln Leu Arg Phe Cys Leu Cys Glu<br>130                         135                       140 | 432 |
| acc agc tgc ccc cag gaa gat tat ttt ccc ccc aac ctc ttt gtc aag<br>Thr Ser Cys Pro Gln Glu Asp Tyr Phe Pro Pro Asn Leu Phe Val Lys<br>145                       150                          155                      160 | 480 |
| gtt aat ggg aaa ctg tgc ccc ctg ccg ggt tac ctt ccc cca acc aag<br>Val Asn Gly Lys Leu Cys Pro Leu Pro Gly Tyr Leu Pro Pro Thr Lys<br>               165                       170                       175 | 528 |
| aat ggg gcc gag ccc aag agg ccc agc cgc ccc atc aac atc aca ccc<br>Asn Gly Ala Glu Pro Lys Arg Pro Ser Arg Pro Ile Asn Ile Thr Pro<br>             180                         185                       190 | 576 |
| ctg gct cga ctc tca gcc act gtt ccc aac acc att gtg gtc aat tgg<br>Leu Ala Arg Leu Ser Ala Thr Val Pro Asn Thr Ile Val Val Asn Trp<br>         195                       200                       205 | 624 |
| tca tct gag ttc gga cgg aat tac tcc ttg tct gtg tac ctg gtg agg<br>Ser Ser Glu Phe Gly Arg Asn Tyr Ser Leu Ser Val Tyr Leu Val Arg<br>         210                       215                      220 | 672 |
| cag ttg act gca gga acc ctt cta caa aaa ctc aga gca aag ggt atc<br>Gln Leu Thr Ala Gly Thr Leu Leu Gln Lys Leu Arg Ala Lys Gly Ile<br>225                       230                         235                      240 | 720 |
| cgg aac cca gac cac tcg cgg gca ctg atc aag gag aaa ttg act gct<br>Arg Asn Pro Asp His Ser Arg Ala Leu Ile Lys Glu Lys Leu Thr Ala<br>             245                         250                       255 | 768 |
| gac cct gac agt gag gtg gcc act aca agt ctc cgg gtg tca ctc atg<br>Asp Pro Asp Ser Glu Val Ala Thr Thr Ser Leu Arg Val Ser Leu Met<br>         260                       265                       270 | 816 |
| tgc ccg cta ggg aag atg cgc ctg act gtc cct tgt cgt gcc ctc acc<br>Cys Pro Leu Gly Lys Met Arg Leu Thr Val Pro Cys Arg Ala Leu Thr<br>             275                         280                       285 | 864 |
| tgt gcc cac ctg cag agc ttc gat gct gcc ctt tat cta cag atg aat<br>Cys Ala His Leu Gln Ser Phe Asp Ala Ala Leu Tyr Leu Gln Met Asn<br>         290                       295                      300 | 912 |
| gag aag aag cct aca tgg aca tgt cct gtg tgt gac aag aag gct ccc<br>Glu Lys Lys Pro Thr Trp Thr Cys Pro Val Cys Asp Lys Lys Ala Pro<br>305                       310                         315                      320 | 960 |
| tat gaa tct ctt atc att gat ggt tta ttt atg gag att ctt agt tcc<br>Tyr Glu Ser Leu Ile Ile Asp Gly Leu Phe Met Glu Ile Leu Ser Ser<br>             325                         330                      335 | 1008 |
| tgt tca gat tgt gat gag atc caa ttc atg gaa gat gga tcc tgg tgc<br>Cys Ser Asp Cys Asp Glu Ile Gln Phe Met Glu Asp Gly Ser Trp Cys<br>         340                       345                      350 | 1056 |
| cca atg aaa ccc aag aag gag gca tct gag gtt tgc ccc ccg cca ggg<br>Pro Met Lys Pro Lys Lys Glu Ala Ser Glu Val Cys Pro Pro Pro Gly<br>             355                         360                       365 | 1104 |
| tat ggg ctg gat ggc ctc cag tac agc cca gtc cag ggg gga gat cca<br>Tyr Gly Leu Asp Gly Leu Gln Tyr Ser Pro Val Gln Gly Gly Asp Pro<br>         370                       375                      380 | 1152 |
| tca gag aat aag aag aag gtc gaa gtt att gac ttg aca ata gaa agc<br>Ser Glu Asn Lys Lys Lys Val Glu Val Ile Asp Leu Thr Ile Glu Ser<br>385                       390                         395                      400 | 1200 |
| tca tca gat gag gag gat ctg ccc cct acc aag aag cac tgt tct gtc<br>Ser Ser Asp Glu Glu Asp Leu Pro Pro Thr Lys Lys His Cys Ser Val<br>             405                         410                       415 | 1248 |
| acc tca gct gcc atc ccg gcc cta cct gga agc aaa gga gtc ctg aca | 1296 |

```
                                                             Thr Ser Ala Ala Ile Pro Ala Leu Pro Gly Ser Lys Gly Val Leu Thr
                                                                         420                 425                 430 tct ggc cac cag cca tcc tcg gtg cta agg agc cct gct atg ggc acg          1344
Ser Gly His Gln Pro Ser Ser Val Leu Arg Ser Pro Ala Met Gly Thr
            435                 440                 445 ttg ggt ggg gat ttc ctg tcc agt ctc cca cta cat gag tac cca cct          1392
Leu Gly Gly Asp Phe Leu Ser Ser Leu Pro Leu His Glu Tyr Pro Pro
450                 455                 460 gcc ttc cca ctg gga gcc gac atc caa ggt tta gat tta ttt tca ttt          1440
Ala Phe Pro Leu Gly Ala Asp Ile Gln Gly Leu Asp Leu Phe Ser Phe
465                 470                 475                 480 ctt cag aca gag agt cag cac tat ggc ccc tct gtc atc acc tca cta          1488
Leu Gln Thr Glu Ser Gln His Tyr Gly Pro Ser Val Ile Thr Ser Leu
                485                 490                 495 gat gaa cag gat gcc ctt ggc cac ttc ttc cag tac cga ggg acc cct          1536
Asp Glu Gln Asp Ala Leu Gly His Phe Phe Gln Tyr Arg Gly Thr Pro
            500                 505                 510 tct cac ttt ctg ggc cca ctg gcc ccc acg ctg ggg agc tcc cac tgc          1584
Ser His Phe Leu Gly Pro Leu Ala Pro Thr Leu Gly Ser Ser His Cys
        515                 520                 525 agc gcc act ccg gcg ccc cct cct ggc cgt gtc agc agc att gtg gcc          1632
Ser Ala Thr Pro Ala Pro Pro Pro Gly Arg Val Ser Ser Ile Val Ala
530                 535                 540 cct ggg ggg gcc ttg agg gag ggg cat gga gga ccc ctg ccc tca ggt          1680
Pro Gly Gly Ala Leu Arg Glu Gly His Gly Gly Pro Leu Pro Ser Gly
545                 550                 555                 560 ccc tct ttg act ggc tgt cgg tca gac atc att tcc ctg gac tga              1725
Pro Ser Leu Thr Gly Cys Arg Ser Asp Ile Ile Ser Leu Asp
                565                 570

<210> SEQ ID NO 4
<211> LENGTH: 574
<212> TYPE: PRT
<213> ORGANISM: Homo sapiens

<400> SEQUENCE: 4

Met Lys Ile Lys Glu Leu Tyr Arg Arg Arg Phe Pro Arg Lys Thr Leu
1               5                   10                  15

Gly Pro Ser Asp Leu Ser Leu Leu Ser Leu Pro Pro Gly Thr Ser Pro
            20                  25                  30

Val Gly Ser Pro Gly Pro Leu Ala Pro Ile Pro Pro Thr Leu Leu Ala
        35                  40                  45

Pro Gly Thr Leu Leu Gly Pro Lys Arg Glu Val Asp Met His Pro Pro
    50                  55                  60

Leu Pro Gln Pro Val His Pro Asp Val Thr Met Lys Pro Leu Pro Phe
65                  70                  75                  80

Tyr Glu Val Tyr Gly Glu Leu Ile Arg Pro Thr Thr Leu Ala Ser Thr
                85                  90                  95

Ser Ser Gln Arg Phe Glu Glu Ala His Phe Thr Phe Ala Leu Thr Pro
            100                 105                 110

Gln Gln Val Gln Gln Ile Leu Thr Ser Arg Glu Val Leu Pro Gly Ala
        115                 120                 125

Lys Cys Asp Tyr Thr Ile Gln Val Gln Leu Arg Phe Cys Leu Cys Glu
    130                 135                 140

Thr Ser Cys Pro Gln Glu Asp Tyr Phe Pro Pro Asn Leu Phe Val Lys
145                 150                 155                 160

Val Asn Gly Lys Leu Cys Pro Leu Pro Gly Tyr Leu Pro Pro Thr Lys
                165                 170                 175
```

-continued

```
Asn Gly Ala Glu Pro Lys Arg Pro Ser Arg Pro Ile Asn Ile Thr Pro
            180                 185                 190
Leu Ala Arg Leu Ser Ala Thr Val Pro Asn Thr Ile Val Val Asn Trp
        195                 200                 205
Ser Ser Glu Phe Gly Arg Asn Tyr Ser Leu Ser Val Tyr Leu Val Arg
    210                 215                 220
Gln Leu Thr Ala Gly Thr Leu Leu Gln Lys Leu Arg Ala Lys Gly Ile
225                 230                 235                 240
Arg Asn Pro Asp His Ser Arg Ala Leu Ile Lys Glu Lys Leu Thr Ala
                245                 250                 255
Asp Pro Asp Ser Glu Val Ala Thr Thr Ser Leu Arg Val Ser Leu Met
            260                 265                 270
Cys Pro Leu Gly Lys Met Arg Leu Thr Val Pro Cys Arg Ala Leu Thr
        275                 280                 285
Cys Ala His Leu Gln Ser Phe Asp Ala Ala Leu Tyr Leu Gln Met Asn
    290                 295                 300
Glu Lys Lys Pro Thr Trp Thr Cys Pro Val Cys Asp Lys Lys Ala Pro
305                 310                 315                 320
Tyr Glu Ser Leu Ile Ile Asp Gly Leu Phe Met Glu Ile Leu Ser Ser
                325                 330                 335
Cys Ser Asp Cys Asp Glu Ile Gln Phe Met Glu Asp Gly Ser Trp Cys
            340                 345                 350
Pro Met Lys Pro Lys Lys Glu Ala Ser Glu Val Cys Pro Pro Pro Gly
        355                 360                 365
Tyr Gly Leu Asp Gly Leu Gln Tyr Ser Pro Val Gln Gly Gly Asp Pro
    370                 375                 380
Ser Glu Asn Lys Lys Lys Val Glu Val Ile Asp Leu Thr Ile Glu Ser
385                 390                 395                 400
Ser Ser Asp Glu Glu Asp Leu Pro Pro Thr Lys His Cys Ser Val
                405                 410                 415
Thr Ser Ala Ala Ile Pro Ala Leu Pro Gly Ser Lys Gly Val Leu Thr
            420                 425                 430
Ser Gly His Gln Pro Ser Ser Val Leu Arg Ser Pro Ala Met Gly Thr
        435                 440                 445
Leu Gly Gly Asp Phe Leu Ser Ser Leu Pro Leu His Glu Tyr Pro Pro
    450                 455                 460
Ala Phe Pro Leu Gly Ala Asp Ile Gln Gly Leu Asp Leu Phe Ser Phe
465                 470                 475                 480
Leu Gln Thr Glu Ser Gln His Tyr Gly Pro Ser Val Ile Thr Ser Leu
                485                 490                 495
Asp Glu Gln Asp Ala Leu Gly His Phe Phe Gln Tyr Arg Gly Thr Pro
            500                 505                 510
Ser His Phe Leu Gly Pro Leu Ala Pro Thr Leu Gly Ser Ser His Cys
        515                 520                 525
Ser Ala Thr Pro Ala Pro Pro Gly Arg Val Ser Ser Ile Val Ala
    530                 535                 540
Pro Gly Gly Ala Leu Arg Glu Gly His Gly Gly Pro Leu Pro Ser Gly
545                 550                 555                 560
Pro Ser Leu Thr Gly Cys Arg Ser Asp Ile Ile Ser Leu Asp
                565                 570

<210> SEQ ID NO 5
<211> LENGTH: 99
```

```
<212> TYPE: PRT
<213> ORGANISM: Rattus norvegicus

<400> SEQUENCE: 5

Thr Trp Thr Cys Pro Val Cys Asp Lys Lys Ala Pro Tyr Glu Ser Leu
1               5                   10                  15

Ile Ile Asp Gly Leu Phe Met Glu Ile Leu Ser Ser Cys Ser Asp Cys
            20                  25                  30

Asp Glu Ile Gln Phe Met Glu Asp Gly Ser Trp Cys Pro Met Lys Pro
        35                  40                  45

Lys Lys Glu Ala Ser Glu Val Cys Pro Pro Pro Gly Tyr Gly Leu Asp
    50                  55                  60

Gly Leu Gln Tyr Ser Pro Val Gln Gly Gly Asp Pro Ser Glu Asn Lys
65                  70                  75                  80

Lys Lys Val Glu Val Ile Asp Leu Thr Ile Glu Ser Ser Ser Asp Glu
                85                  90                  95

Glu Asp Leu

<210> SEQ ID NO 6
<211> LENGTH: 572
<212> TYPE: PRT
<213> ORGANISM: Homo sapiens
<220> FEATURE:
<221> NAME/KEY: misc_feature
<222> LOCATION: (41)..(41)
<223> OTHER INFORMATION: Xaa = proline or serine
<221> NAME/KEY: misc_feature
<222> LOCATION: (48)..(48)
<223> OTHER INFORMATION: Xaa = alanine or threonine
<221> NAME/KEY: misc_feature
<222> LOCATION: (115)..(115)
<223> OTHER INFORMATION: Xaa = valine or leucine
<221> NAME/KEY: misc_feature
<222> LOCATION: (335)..(335)
<223> OTHER INFORMATION: Xaa = serine or asparagine
<221> NAME/KEY: misc_feature
<222> LOCATION: (381)..(381)
<223> OTHER INFORMATION: Xaa = glycine or glutamic acid
<221> NAME/KEY: misc_feature
<222> LOCATION: (383)..(383)
<223> OTHER INFORMATION: Xaa = aspartic acid or asparagine
<221> NAME/KEY: misc_feature
<222> LOCATION: (384)..(384)
<223> OTHER INFORMATION: Xaa = isoproline or glutamine
<221> NAME/KEY: misc_feature
<222> LOCATION: (390)..(390)
<223> OTHER INFORMATION: Xaa = lysine or arganine
<221> NAME/KEY: misc_feature
<222> LOCATION: (416)..(416)
<223> OTHER INFORMATION: Xaa = serine or proline
<221> NAME/KEY: misc_feature
<222> LOCATION: (431)..(431)
<223> OTHER INFORMATION: Xaa = valine or alanine
<221> NAME/KEY: misc_feature
<222> LOCATION: (451)..(451)
<223> OTHER INFORMATION: Xaa = glycine or serine
<221> NAME/KEY: misc_feature
<222> LOCATION: (489)..(489)
<223> OTHER INFORMATION: Xaa = glycine or serine
<221> NAME/KEY: misc_feature
<222> LOCATION: (501)..(501)
<223> OTHER INFORMATION: Xaa = alanine or threonine
<221> NAME/KEY: misc_feature
<222> LOCATION: (508)..(508)
<223> OTHER INFORMATION: Xaa = tyrosine or phenylalanine
<221> NAME/KEY: misc_feature
<222> LOCATION: (513)..(513)
<223> OTHER INFORMATION: Xaa = serine or proline
<221> NAME/KEY: misc_feature
<222> LOCATION: (528)..(528)
<223> OTHER INFORMATION: Xaa = cysteine or arginine
```

```
<221> NAME/KEY: misc_feature
<222> LOCATION: (535)..(535)
<223> OTHER INFORMATION: Xaa = proline or alanine
<221> NAME/KEY: misc_feature
<222> LOCATION: (547)..(547)
<223> OTHER INFORMATION: Xaa = glycine or serine
<221> NAME/KEY: misc_feature
<222> LOCATION: (548)..(548)
<223> OTHER INFORMATION: Xaa = alanine or serine
<221> NAME/KEY: misc_feature
<222> LOCATION: (570)..(570)
<223> OTHER INFORMATION: Xaa = isoleucine or valine

<400> SEQUENCE: 6

Met Lys Ile Lys Glu Leu Tyr Arg Arg Phe Pro Arg Lys Thr Leu
1               5                   10                  15

Gly Pro Ser Asp Leu Ser Leu Leu Ser Leu Pro Pro Gly Thr Ser Pro
                20                  25                  30

Val Gly Ser Pro Xaa Pro Leu Ala Xaa Ile Pro Pro Thr Leu Leu Xaa
            35                  40                  45

Pro Gly Thr Leu Leu Gly Pro Lys Arg Glu Val Asp Met His Pro Pro
50                  55                  60

Leu Pro Gln Pro Val His Pro Asp Val Thr Met Lys Pro Leu Pro Phe
65                  70                  75                  80

Tyr Glu Val Tyr Gly Glu Leu Ile Arg Pro Thr Thr Leu Ala Ser Thr
                85                  90                  95

Ser Ser Gln Arg Phe Glu Glu Ala His Phe Thr Phe Ala Leu Thr Pro
                100                 105                 110

Gln Gln Xaa Gln Gln Ile Leu Thr Ser Arg Glu Val Leu Pro Gly Ala
            115                 120                 125

Lys Leu Asp Tyr Thr Ile Gln Val Gln Leu Arg Phe Cys Leu Cys Glu
130                 135                 140

Thr Ser Leu Pro Gln Glu Asp Tyr Phe Pro Pro Asn Leu Phe Val Lys
145                 150                 155                 160

Val Asn Gly Lys Leu Cys Pro Leu Pro Gly Tyr Leu Pro Pro Thr Lys
                165                 170                 175

Asn Gly Ala Glu Pro Lys Arg Pro Ser Arg Pro Ile Asn Ile Thr Pro
                180                 185                 190

Lys Ala Arg Leu Ser Ala Thr Val Pro Asn Thr Ile Val Val Asn Trp
                195                 200                 205

Ser Ser Glu Phe Gly Arg Asn Thr Ser Leu Ser Val Tyr Leu Val Arg
210                 215                 220

Gln Leu Thr Ala Gly Thr Leu Gln Lys Leu Arg Ala Lys Gly Ile
225                 230                 235                 240

Arg Asn Pro Asp His Ser Arg Ala Leu Ile Lys Gly Lys Leu Thr Ala
                245                 250                 255

Asp Pro Asp Ser Gly Val Ala Thr Thr Ser Leu Arg Val Ser Leu Met
                260                 265                 270

Cys Pro Leu Gly Lys Met Arg Leu Thr Val Pro Cys Arg Ala Leu Thr
                275                 280                 285

Cys Ala His Leu Gln Ser Phe Ser Ala Ala Leu Tyr Leu Gln Met Asn
                290                 295                 300

Glu Lys Pro Thr Trp Thr Cys Pro Val Cys Asp Lys Lys Ala Pro Trp
305                 310                 315                 320

Glu Ser Leu Ile Ile Asp Gly Leu Phe Met Glu Ile Leu Xaa Ser Cys
                325                 330                 335

Ser Asp Cys Asp Glu Ile Gln Phe Met Glu Asp Gly Ser Thr Cys Pro
```

```
                     340                 345                 350
Met Lys Pro Lys Lys Glu Ala Ser Glu Val Cys Pro Pro Gly Tyr
                355                 360                 365

Gly Leu Asp Gly Leu Gln Tyr Ser Pro Val Gln Xaa Gly Xaa Pro Ser
    370                 375                 380

Glu Asn Lys Lys Xaa Val Glu Val Ile Asp Leu Thr Ile Glu Ser Ser
385                 390                 395                 400

Ser Asp Glu Glu Asp Leu Pro Pro Thr Lys Lys His Cys Xaa Val Thr
                405                 410                 415

Ser Ala Ala Ile Pro Ala Leu Pro Gly Ser Lys Gly Xaa Leu Thr Ser
                420                 425                 430

Gly His Gln Pro Ser Ser Val Leu Arg Ser Pro Ala Met Gly Thr Leu
                435                 440                 445

Gly Xaa Asp Phe Leu Ser Ser Leu Pro Leu His Glu Tyr Pro Pro Ala
    450                 455                 460

Phe Pro Leu Gly Ala Asp Ile Gln Gly Leu Asp Leu Phe Ser Phe Leu
465                 470                 475                 480

Gln Thr Glu Ser Gln Tyr Xaa Pro Ser Val Ile Thr Ser Leu Asp Glu
                485                 490                 495

Gln Asp Xaa Leu Gly His Phe Phe Gln Xaa Arg Phe Thr Pro Xaa His
                500                 505                 510

Phe Leu Gly Pro Leu Ala Pro Thr Leu Gly Ser Ser His Xaa Ser Ala
                515                 520                 525

Thr Pro Ala Pro Xaa Pro Gly Arg Val Ser Ser Ile Val Ala Pro Gly
                530                 535                 540

Xaa Xaa Leu Arg Glu Gly His Gly Gly Pro Leu Pro Ser Gly Pro Ser
545                 550                 555                 560

Leu Thr Gly Cys Arg Ser Asp Ile Xaa Ser Leu Asp
                565                 570

<210> SEQ ID NO 7
<211> LENGTH: 99
<212> TYPE: PRT
<213> ORGANISM: Homo sapiens

<400> SEQUENCE: 7

Thr Trp Thr Cys Pro Val Cys Asp Lys Lys Ala Pro Tyr Glu Ser Leu
1               5                   10                  15

Ile Ile Asp Gly Leu Phe Met Glu Ile Leu Asn Ser Cys Ser Asp Cys
                20                  25                  30

Asp Glu Ile Gln Phe Met Glu Asp Gly Ser Trp Cys Pro Met Lys Pro
            35                  40                  45

Lys Lys Glu Ala Ser Glu Val Cys Pro Pro Gly Tyr Gly Leu Asp
        50                  55                  60

Gly Leu Gln Tyr Ser Pro Val Gln Glu Gly Asn Gln Ser Glu Asn Lys
65                  70                  75                  80

Lys Arg Val Glu Val Ile Asp Leu Thr Ile Glu Ser Ser Asp Glu
                85                  90                  95

Glu Asp Leu

<210> SEQ ID NO 8
<211> LENGTH: 167
<212> TYPE: PRT
<213> ORGANISM: Homo sapiens

<400> SEQUENCE: 8
```

```
Pro Pro Thr Lys Lys His Cys Ser Val Thr Ser Ala Ala Ile Pro Ala
 1               5                  10                  15

Leu Pro Gly Ser Lys Gly Val Leu Thr Ser Gly His Gln Pro Ser Ser
            20                  25                  30

Val Leu Arg Ser Pro Ala Met Gly Thr Leu Gly Gly Asp Phe Leu Ser
        35                  40                  45

Ser Leu Pro Leu His Glu Tyr Pro Pro Ala Phe Pro Leu Gly Ala Asp
    50                  55                  60

Ile Gln Gly Leu Asp Leu Phe Ser Phe Leu Gln Thr Glu Ser Gln His
65                  70                  75                  80

Tyr Gly Pro Ser Val Ile Thr Ser Leu Asp Glu Gln Asp Ala Leu Gly
                85                  90                  95

His Phe Phe Gln Tyr Arg Gly Thr Pro Ser His Phe Leu Gly Pro Leu
                100                 105                 110

Ala Pro Thr Leu Gly Ser Ser His Cys Ser Ala Thr Pro Ala Pro Pro
            115                 120                 125

Pro Gly Ala Val Ser Ser Ile Val Ala Pro Gly Ala Leu Arg Glu
            130                 135                 140

Gly His Gly Gly Pro Leu Pro Ser Gly Pro Ser Leu Thr Gly Cys Arg
145                 150                 155                 160

Ser Asp Ile Ile Ser Leu Asp
                165
```

<210> SEQ ID NO 9
<211> LENGTH: 167
<212> TYPE: PRT
<213> ORGANISM: Homo sapiens

<400> SEQUENCE: 9

```
Pro Pro Thr Lys Lys His Cys Pro Val Thr Ser Ala Ala Ile Pro Ala
 1               5                  10                  15

Leu Pro Gly Ser Lys Gly Ala Leu Thr Ser Gly His Gln Pro Ser Ser
            20                  25                  30

Val Leu Arg Ser Pro Ala Met Gly Thr Leu Gly Ser Asp Phe Leu Ser
        35                  40                  45

Ser Leu Pro Leu His Glu Tyr Pro Pro Ala Phe Pro Leu Gly Ala Asp
    50                  55                  60

Ile Gln Gly Leu Asp Leu Phe Ser Phe Leu Gln Thr Glu Ser Gln His
65                  70                  75                  80

Tyr Ser Pro Ser Val Ile Thr Ser Leu Asp Glu Gln Asp Thr Leu Gly
                85                  90                  95

His Phe Phe Gln Phe Arg Gly Thr Pro Pro His Phe Leu Gly Pro Leu
                100                 105                 110

Ala Pro Thr Leu Gly Ser Ser His Arg Ser Ala Thr Pro Ala Pro Ala
            115                 120                 125

Pro Gly Arg Val Ser Ser Ile Val Ala Pro Gly Ser Ser Leu Arg Glu
            130                 135                 140

Gly His Gly Gly Pro Leu Pro Ser Gly Pro Ser Leu Thr Gly Cys Arg
145                 150                 155                 160

Ser Asp Val Ile Ser Leu Asp
                165
```

<210> SEQ ID NO 10
<211> LENGTH: 98
<212> TYPE: PRT

```
<213> ORGANISM: synthetic construct
<220> FEATURE:
<221> NAME/KEY: misc_feature
<222> LOCATION: (25)..(25)
<223> OTHER INFORMATION: Xaa = serine or asparagine
<221> NAME/KEY: misc_feature
<222> LOCATION: (61)..(61)
<223> OTHER INFORMATION: Xaa = glycine or glutamic acid
<221> NAME/KEY: misc_feature
<222> LOCATION: (63)..(63)
<223> OTHER INFORMATION: Xaa = aspartic acid or asparagine
<221> NAME/KEY: misc_feature
<222> LOCATION: (64)..(64)
<223> OTHER INFORMATION: Xaa = proline or glutamine

<400> SEQUENCE: 10

Trp Thr Cys Pro Val Cys Asp Lys Lys Ala Pro Tyr Glu Ser Leu Ile
1               5                  10                  15

Ile Asp Gly Leu Phe Met Glu Ile Leu Xaa Ser Cys Ser Asp Cys Asp
                20                  25                  30

Glu Ile Gln Phe Met Glu Asp Gly Ser Trp Leu Pro Met Lys Pro Lys
            35                  40                  45

Lys Glu Ala Ser Glu Val Cys Pro Pro Gly Tyr Gly Leu Asp Gly
50                  55                  60

Leu Gln Tyr Ser Pro Val Gln Xaa Gly Xaa Pro Ser Glu Asn Lys Lys
65                  70                  75                  80

Xaa Val Glu Val Ile Asp Leu Thr Ile Glu Ser Ser Ser Asp Glu Glu
                85                  90                  95

Asp Leu

<210> SEQ ID NO 11
<211> LENGTH: 167
<212> TYPE: PRT
<213> ORGANISM: Rattus norvegicus
<220> FEATURE:
<221> NAME/KEY: misc_feature
<222> LOCATION: (8)..(8)
<223> OTHER INFORMATION: Xaa = serine or proline
<221> NAME/KEY: misc_feature
<222> LOCATION: (23)..(23)
<223> OTHER INFORMATION: Xaa = valine or alanine
<221> NAME/KEY: misc_feature
<222> LOCATION: (44)..(44)
<223> OTHER INFORMATION: Xaa = glycine or serine
<221> NAME/KEY: misc_feature
<222> LOCATION: (82)..(82)
<223> OTHER INFORMATION: Xaa = glycine or serine
<221> NAME/KEY: misc_feature
<222> LOCATION: (94)..(94)
<223> OTHER INFORMATION: Xaa = alanine or threonine
<221> NAME/KEY: misc_feature
<222> LOCATION: (101)..(101)
<223> OTHER INFORMATION: Xaa = tyrosine or phenylalanine
<221> NAME/KEY: misc_feature
<222> LOCATION: (106)..(106)
<223> OTHER INFORMATION: Xaa = serine or proline
<221> NAME/KEY: misc_feature
<222> LOCATION: (121)..(121)
<223> OTHER INFORMATION: Xaa = cysteine or alanine
<221> NAME/KEY: misc_feature
<222> LOCATION: (128)..(128)
<223> OTHER INFORMATION: Xaa = proline or alanine
<221> NAME/KEY: misc_feature
<222> LOCATION: (140)..(140)
<223> OTHER INFORMATION: Xaa = glycine or serine
<221> NAME/KEY: misc_feature
<222> LOCATION: (141)..(141)
<223> OTHER INFORMATION: Xaa = alanine or serine
<221> NAME/KEY: misc_feature
<222> LOCATION: (164)..(164)
<223> OTHER INFORMATION: Xaa = isoleucine or valine
```

```
<400> SEQUENCE: 11

Pro Pro Thr Lys Lys His Cys Xaa Val Thr Ser Ala Ala Ile Pro Ala
1               5                   10                  15

Leu Pro Gly Ser Lys Gly Xaa Leu Thr Ser Gly His Gln Pro Ser Ser
                20                  25                  30

Val Leu Arg Ser Pro Ala Met Gly Thr Leu Gly Xaa Asp Phe Leu Ser
            35                  40                  45

Ser Leu Pro Leu His Glu Tyr Pro Pro Ala Phe Pro Leu Gly Ala Asp
        50                  55                  60

Ile Gln Gly Leu Asp Leu Phe Ser Phe Leu Gln Thr Glu Ser Gln His
65                  70                  75                  80

Tyr Xaa Pro Ser Val Ile Thr Ser Leu Asp Glu Gln Asp Xaa Leu Gly
                85                  90                  95

His Phe Phe Gln Xaa Arg Gly Thr Pro Xaa His Phe Leu Gly Pro Leu
                100                 105                 110

Ala Pro Thr Leu Gly Ser Ser His Xaa Ser Ala Thr Pro Ala Pro Xaa
            115                 120                 125

Pro Gly Arg Val Ser Ser Ile Val Ala Pro Gly Xaa Xaa Leu Arg Glu
        130                 135                 140

Gly His Gly Gly Pro Leu Pro Ser Gly Pro Ser Leu Thr Gly Cys Arg
145                 150                 155                 160

Ser Asp Ile Xaa Ser Leu Asp
                165

<210> SEQ ID NO 12
<211> LENGTH: 26
<212> TYPE: PRT
<213> ORGANISM: Rattus norvegicus

<400> SEQUENCE: 12

Ala Thr Gly Ala Ala Gly Ala Thr Cys Ala Ala Gly Ala Gly Cys
1               5                   10                  15

Thr Thr Thr Ala Cys Cys Gly Ala Cys Gly
                20                  25

<210> SEQ ID NO 13
<211> LENGTH: 23
<212> TYPE: PRT
<213> ORGANISM: Rattus norvegicus

<400> SEQUENCE: 13

Thr Cys Ala Gly Thr Cys Cys Ala Gly Gly Gly Ala Ala Ala Thr Cys
1               5                   10                  15

Ala Thr Gly Ala Cys Cys Gly
                20
```